United States Patent
Musick

(10) Patent No.: US 7,527,971 B2
(45) Date of Patent: May 5, 2009

(54) ADULT STEM CELL LINES

(75) Inventor: James R. Musick, Conifer, CO (US)

(73) Assignee: Vitro Diagnostics, Inc., Golden, CO (US)

(*) Notice: Subject to any disclaimer, the term of this patent is extended or adjusted under 35 U.S.C. 154(b) by 13 days.

(21) Appl. No.: 11/256,673

(22) Filed: Oct. 20, 2005

(65) Prior Publication Data

US 2006/0093586 A1   May 4, 2006

Related U.S. Application Data

(60) Provisional application No. 60/620,838, filed on Oct. 20, 2004, provisional application No. 60/664,388, filed on Mar. 22, 2005.

(51) Int. Cl.
C12N 5/00 (2006.01)
C12N 5/08 (2006.01)
A01N 63/00 (2006.01)
A01N 65/00 (2006.01)

(52) U.S. Cl. ........................ 435/325; 435/366; 435/375; 435/377; 424/93.1; 424/93.7

(58) Field of Classification Search ........................ None
See application file for complete search history.

(56) References Cited

U.S. PATENT DOCUMENTS 5,629,159 A    5/1997    Anderson 6,458,593 B1    10/2002    Musick et al.
2003/0059897 A1    3/2003    Musick et al.

FOREIGN PATENT DOCUMENTS

| FR | 2681609 | 3/1993 |
| WO | WO 98/56393 | 12/1998 |
| WO | WO 99/35245 | 7/1999 |
| WO | WO 99/37752 | 7/1999 |
| WO | WO 2004/050827 | * 6/2004 |

OTHER PUBLICATIONS

Zhou et al., 2002, Journal of cellular Physiology 192: 304-314.*
Yao et al., 2004, World Journal of Gastroenterology 10:1452-1456.*
Chen et al., 2004, World Journal of Gastroenterology 10:3016-3020.*
Santana et al., 2006, J. Cell. Mol. Med. 10:866-883.*
Seaberg et al., 2004, Nature Biotechnology 22:1115-1124.*
Hebrok et al., 2003, Mechanisms of Development 120:45-57.*
Omer et al., 2003, Diabetes 52:6975.*
Bonner-Weir et al., 2002, Journal of Pathology 197: 519-526.*

(Continued)

*Primary Examiner*—Robert M Kelly
*Assistant Examiner*—Kelaginamane Hiriyanna
(74) *Attorney, Agent, or Firm*—Kristine H. Johnson; Dickinson Wright, PLLC

(57) ABSTRACT

The present invention is directed to a new cell line, VIT4-G9, which has been deposited as ATCC Accession number PTA-8683.

1 Claim, 5 Drawing Sheets

OTHER PUBLICATIONS

Di Simone et al., c-Ha-ras transfection and expression of MDR-related genese in MCF-10A human breast cell line. Anticancer Research, 1997; vol. 17, pp. 3587-3592.
Edelstein et al., Diabetologia, 41:736-739 (1998).
Evrard et al., 1988, J. Neuroscience Res., 21:80-87.
Falchetti et al., Oncogene, 18:1515-1519 (1999).
Ham et al., J. Clin. Endocrinol., 83(5):1598-1603 (1998).
Hayward et al., 1995, In Vitro Cell Dev. Biolo., 31A:14-24.
Ishii et al., 1992, Cell Structure and Function, 17:197-202.
Mothersill et al., Expression of delayed toxicity and lethal mutations in the progeny of human cells surviving exposure to radiation and other environmental mutagens. Int. J. Radiat. Biol. 1998; vol. 74, pp. 673-680.
Offord et al., Invest. Opthalmol. Vis. Sci., 40:1091-1101 (1999).
Prasad et al., In Vitro Cell. Dev. Biol., 30A(9):596-603 (1994).
Raymon et al., J. Neurosci., 19(13):5420-5428 (1999).
Stapleton et al., Oncogene, 6:807-818 (1991) (Abstract).
Examiner's First Report for Australian Patent Application No. 25156/00, mailed Jul. 28, 2003.
Official Action for European Patent Application No. 00903408.3-2401, mailed Jun. 5, 2003.
Official Action for European Patent Application No. 00903408.3-2401, mailed Jun. 14, 2004.
Mayhall et al. "The clinical potential of stem cells", Curr Opin Cell Biol., Dec. 2004, Vo. 16, No. 6, pp. 713-720.
International Search Report for International (PCT) Patent Application No. PCT/US05/38162, mailed May 1, 2008.
Written Opinion for International (PCT) Patent Application No. PCT/US05/38162, mailed May 1, 2008.

* cited by examiner 200 microns

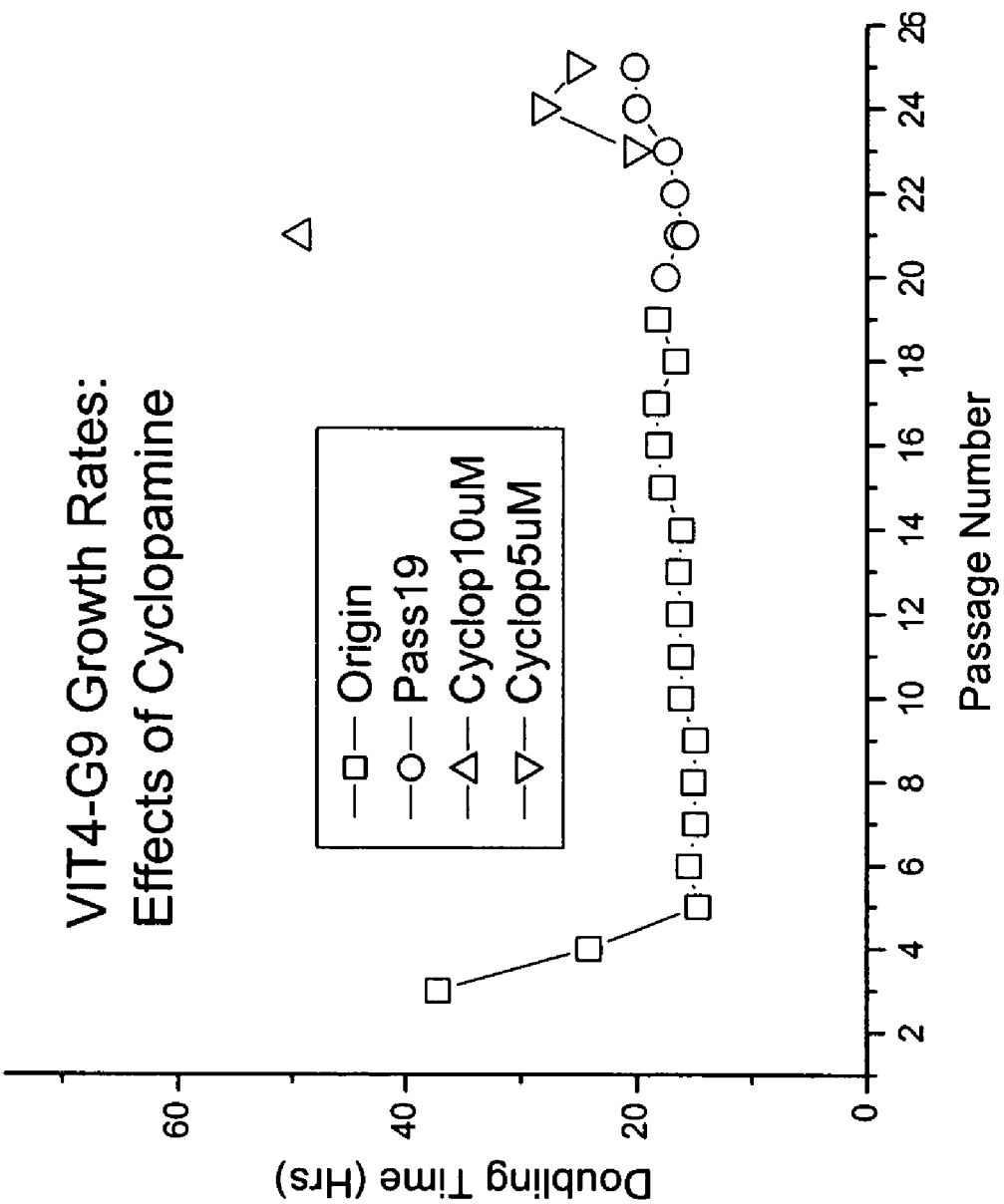

ADULT STEM CELL LINES

CROSS-REFERENCE TO RELATED APPLICATIONS

This application claims the benefit of priority under 35 U.S.C. § 119(e) from U.S. Provisional Application Ser. No. 60/620,838, filed Oct. 20, 2004 and from U.S. Provisional Application Ser. No. 60/664,388, filed Mar. 22, 2005. The entire disclosure of each of U.S. Provisional Application Ser. No. 60/620,838 and U.S. Provisional Application Ser. No. 60/664,388 is incorporated herein by reference in its entirety.

FIELD OF THE INVENTION

The present invention is related to methods of generating stem cell lines from various sources together with methods for the differentiation of these stem cells into terminally differentiated cell types and to cell lines produced by these methods.

BACKGROUND

Endocrine functions of the pancreas gland are performed by a multi-cellular structure known as the islets of Langerhans that are present throughout the pancreas gland. These structures are also known as pancreatic islets, beta islets or pancreatic beta islets. Islets of the adult pancreas are comprised of alpha, beta, delta, pancreatic polypeptide (PP) cells, which are endocrine cells that synthesize and release glucagon, insulin, somatostatin and pancreatic polypeptide respectively. Also, the beta islets contain fibroblast and endothelial cells, the latter comprising blood vessels that permeate the islets. Both insulin and glucagon mediate central roles in carbohydrate metabolism: insulin through promotion of cellular uptake and utilization of glucose and glucagon by its glycogenolytic effect that generates glucose from glycogen.

Type I diabetes mellitus occurs by selective autoimmune destruction of the insulin-producing beta cells of the beta islets. In the late 1990's, Canadian scientists discovered that transplantation of purified beta islets into diabetic patients resulted in insulin independence when islets from at least two donors were transplanted using specific anti-rejection drugs (Shapiro, et al, 2000). The so-called Edmonton protocol has been subject to additional clinical trials now including about 300 transplant recipients. More than half of the transplant recipients were insulin independent one year following transplantation and there was also a significant reduction in diabetes-related complications in the transplant recipients. These findings provide encouragement for finding an effective treatment of type I diabetes mellitus, a debilitating disease affecting about 15 million people worldwide with an increasing rate of incidence. While insulin therapy can regulate blood glucose to normal levels, it is not a cure and many of the life threatening consequences of diabetes eventually strike insulin-treated type I diabetics with enormous medical costs, reducing quality of life and resulting in premature death. Further development of transplantation therapy depends on generation of much larger quantities of human beta cells than are available through organ donation and this is a major goal of diabetes research.

One approach to developing large quantities of beta islets for transplantation is the development of methods to induce stem cells to develop into fully differentiated beta islets suitable for transplantation. Studies of the proliferative capacity of beta islets through in-vitro cell culture indicate that islets do not proliferate and rapidly lose functional properties including insulin content and its secretion in response to elevated glucose concentrations (McEvoy, et al, 1986). There is thus a need for an in-vitro model system of self-renewing stem cells that can be induced to form fully differentiated beta islets, including the constituent cells. The present invention fills this need and other similar applications as well.

The developmental biology of the pancreas organ and especially the endocrine cells comprising beta islets has been extensively studied, and this research indicates clearly that insulin-producing beta cells normally arise from endodermally-derived precursor cells through a complex series of regulatory events involving coordinated expression of a variety of helix-loop-helix transcription factors regulating endoderm establishment and pancreatic determination. The morphogenesis of the pancreas gland as well as epithelial-mesenchymal interactions that are instrumental in pancreas development have also been described (Reviewed by Edlund, 2001 & Jensen, 2004).

SUMMARY OF THE INVENTION

The primary embodiments of the present invention include a new method of generation of adult stem cells with capacity to differentiate into endocrine cells of the pancreas gland comprising the steps of a) obtaining a culture of mesenchymal cells; and b) inducing the expression of epithelial cell markers in the culture of mesenchymal cells; and c) isolating and cloning cells expressing epithelial cell markers; and d) maintaining and expanding the isolated and cloned cells to generate stem cell lines. Further embodiments of the method of stem cell generation pertain to the sources of the mesenchymal cells and the methods of inducing epithelial marker expression. The invention also includes methods to induce differentiation of the stem cell lines into terminally differentiated cell types, especially endocrine cells comprising the Islets of Langerhans. The invention teaches a method of differentiation using a growth phase followed by a differentiation phase under defined environmental conditions. The invention also includes at least 30 different cell lines that were generated using the methods herein elaborated in detail. In general, the invention includes cell lines derived using the new method of stem cell generation that is herein described. Furthermore, the invention includes applications of the stem cells as well as the fully differentiated cells derived there from in the treatment of diabetes in animals and humans through transplantation procedures and associated methods to reduce or eliminate immune rejection of the transplanted cells. Additional embodiments of the invention are also described herein.

BRIEF DESCRIPTION OF DRAWINGS

FIGS. 3A, 3B and 3D are VIT2 cells without ILCC (A) or with a large, diffuse ILCC (C) while in culture. FIG. 3D shows an ILCC from VIT2 cells fixed and stained for insulin (dark deposits) as described in the methods section of example 4. FIG. 3C shows VIT3 cells without any associated ILCCs. ILCC were typically present only after these cultures had reached confluence and slower growth rates.

FIG. 5 shows growth rate analysis of the VIT4-G9 cell line and the effect of 10 (Δ) and 5 (∇) μM cyclopamine. Doubling time in hours is plotted as a function of passage number. The different plots shown reflect the starting passage of the cells either from the $3^{rd}$ passage (origin) or frozen stocks (See legend) that were maintained in liquid nitrogen prior to expansion in culture according to the methods described in example 6. The number of population doublings is calculated as described and discussed in the example 6.

DETAILED DESCRIPTION OF THE INVENTION

Figure 1B:
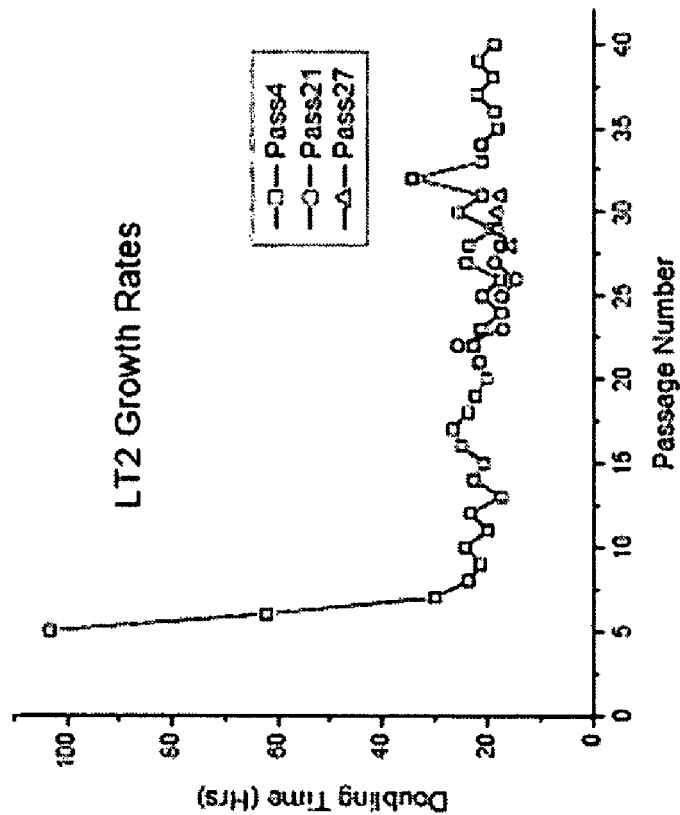
FIGS. 1A and 1B show growth rate analysis of the VIT1 (FIG. 1A) and LT2 (FIG. 1B) cell lines. Doubling time in hours is plotted as a function of passage number. The different plots shown reflect the starting passage of the cells either from the origin of the cell line or frozen stocks (See legend) that were maintained in liquid nitrogen prior to expansion in culture according to the methods described in example 2. The number of population doublings is calculated as described and discussed in the example 2.

The invention described and elaborated herein refers on the one hand to the process of establishing stem and progenitor animal cell lines and their differentiation into a desired cell type and also, to those cell lines derived according to the processes herein described. In the broadest sense, the present invention includes all animal species and fully differentiated cell types and is not limited to any particular species or type of fully differentiated cell. While the present application is exemplified using stem and progenitor cell lines derived from the human pancreas gland that have been specifically induced to form functional human beta cells that comprise human beta islets, this is not intended to limit the scope of the present application and those skilled in the art will recognize that the novel method of stem cell generation and differentiation described herein may be applied to a variety of different tissues, cell lines and other cell sources to generate stem cell lines and differentiate these lines into various functional, fully differentiated cell types.

The present invention arose from the present inventor's initial observations suggesting derivation of insulin-containing beta islet cells from mesenchymal cells in primary cultures of dispersed human fetal pancreas cells. A pancreatic mesenchymal cell line was established that exhibits a profile of expression of both phenotypic and genetic mesenchymal cell markers while lacking expression of markers characteristic of endodermal or epithelial cells. Cells expressing epithelial cell markers, including islet-like cells containing insulin were induced in these mesenchymal cell cultures by exposure to glucagon-like peptide 1 (GLP-1). Isolation and cloning was used to establish lines of cells expressing epithelial markers, which were found to possess properties of stem cells. These include: Self-renewal and apparent immortality, possibly due to the activation of the Wnt and hedgehog signaling pathways since inhibition of hedgehog activation blocked growth, expression of numerous stem cell-specific and homeobox genes and ability to generate islet-like cells expressing both glucagon and insulin. Furthermore, using a specific two-step process, the islet-like cells could be differentiated into functional beta cells as indicated by basal and glucose-regulated insulin secretion. From these results, it is apparent that human pancreatic mesenchymal cells are a source of adult stem cells that are at least multipotent and capable of differentiation into different cells comprising human beta islets.

The present invention was not anticipated based upon the current state of the art regarding the development of the endocrine pancreas gland, wherein it has been shown that beta islet cells are derived from endodermal cells (Edlund, 2001; Jensen, 2004). While developmental pathways do not usually involve a shift in cell types between the three germinal cell types, mesenchymal to epithelium transition (or so-called MET) is an important component of kidney development resulting in the formation of nephrons while the collecting duct system arises by branching of a bud derived from a pre-existing epithelium comparable to other glandular systems (e.g., Davies, 1996; Davies, et al, 1999). However, mesenchyme to epithelium transition is not a previously known mechanism of the development of the pancreas gland or beta islet cellular components. The present invention suggests that a cellular transition from mesenchymal cells to those expressing epithelial markers and stem cell properties may be an important component in development and renewal of pancreatic beta islet cells. Such systems are likely to operate in other organ systems, especially endocrine organs that manufacture and secrete hormones, since a similar system of stem cell generation has been observed in human pituitary cell cultures (Unpublished observation).

The present invention teaches a new process for the generation and differentiation of stem cells. This process arose from research conducted showing that beta islet progenitor cells could be derived from mesenchymal cell cultures using a process involving the induction of epithelial cell markers within the mesenchymal culture, isolation and cloning of the cells expressing epithelial markers and expansion of these cell lines under defined conditions of in-vitro cell culture. About 30 new stem cell lines were derived using the new process of stem cell generation. These cell lines were initially shown to differentiate into beta islet cells that express the pancreatic hormones glucagon and insulin, suggesting that the new stem cell lines were at least multipotent and capable of differentiation into presumptive alpha and beta cells that comprise the human beta islet. This property is also distinct from known developmental processes since beta and delta cell development is coupled through a Pax4-controlled lineage while alpha cells are specified through a different lineage pathway (Edlund, 2001; Jensen, 2004). The differentiation process was subject to further development. It was shown that functional human beta cells, as defined by basal and glucose-stimulated insulin secretion (by both calcium dependent and to a lesser extent by calcium independent mechanisms), could be differentiated from a specific beta islet progenitor cell line using a procedure involving a growth phase followed by a differentiation phase under defined conditions. The new invention thus consists of new procedures for the generation of stem cells combined with procedures to induce differentiation of the stem cells into fully functional specific cell types such as terminally differentiated cells comprising the human beta islet.

The new invention provides advances over the prior state of the art. First, the new invention teaches a reliable method of stem cell generation with application to a wide variety of human and animal tissues. The method has been shown to be reproducible and robust since the examples described herein teach methods that resulted in the generation of about thirty different stem cell lines. Also, since the stem cells derived from the process herein described are readily generated through use of well known methods of in-vitro cell culture, the invention allows detailed study of potential growth and differentiation factors that may be key components of endogenous cell regeneration and renewal processes. Expanded knowledge of such systems may result in the generation of new pharmaceutical agents capable of the activation of endogenous cellular regeneration and renewal processes. An example of such a drug is the incretin hormone mimetic, Exenatide® which is a synthetic version of exendin-4 that is a long-acting analogue of GLP-1. Exendin-4 and Exenatide® have endocrinotrophic effects, possibly including activation of the processes herein described, that induce generation of human beta cells. When coupled together with other procedures that block or disable autoimmune destruction of pancreatic beta cells or re-establish insulin responsiveness, the regeneration of functional pancreatic endocrine systems in those patients afflicted with diabetes mellitus becomes a possibility.

Also, a key issue in stem cell biology is the identification of cell surface markers that are unique to stem cells, e.g., $CD_{34}$ in combination with or without other cluster designation molecules. Since the present invention provides a reliable and straightforward method of stem cell generation, it may be applied to additional investigation of stem cell marker profiles and thus contribute to understanding of the unique molecular expression of adult stem cells. Such markers may valuable tools in advancing stem cell biology. The present invention also provides a reliable and indefinite supply of specific terminally differentiated cell types with numerous medical applications. For example, terminally differentiated cells may allow generation of large-scale quantities of cellular products including secreted pituitary hormones that are identical to native hormones in isoform profile and other biological properties since products are derived from cells that produce these molecules in-vivo. Also, terminally differentiated cells may be used in various cell therapeutic applications as described in greater detail below. Furthermore, the present invention allows more detailed investigation into the role of mesenchyme to epithelial transition in the development, renewal and regeneration of biological systems. While it has long been recognized that secreted factors of mesenchymal cells, e.g., BMPs, are critical regulatory factors in the development of many organ systems, the present invention suggests that mesenchyme to epithelial transition may be a more widespread mechanism of cellular development, regeneration and renewal.

The following terms are used to describe the present invention; these terms are defined as follows: a) Stem cells are immortal cells that can differentiate into multiple or single cell types with specific phenotypic properties such as bone or muscle cells when exposed to specific environmental conditions. b) Embryonic stem cells are pluripotent, meaning that these cells are capable of differentiation into several different types of cells. c) Adult stem cells or progenitor cells, as used herein, are capable of differentiation into more limited cell types, usually the various types of cells that comprise an organ, such as, for example, the lactotropes, thyrotropes, gonadotropes and somatotropes of the pituitary gland. d) Immortality as used herein describes the lifetime capacity of a cell line and refers to a cell line capable of expansion beyond 50 population doublings, the growth span of mortal cells (Hayflick, 1985), and secondary senescence. Cell lines capable of expansion through at least 100 population doublings are defined as immortal herein. e) Self-renewal as used herein refers to an immortalized cell line that can be differentiated into a specific cell phenotype in response to specific environmental conditions. f) Secondary senescence refers to a crisis stage occurring at greater than 50 population doublings resulting in senescence of a cell line and cessation of its proliferative capacity, due in part to reduced telomerase activity. g) Beta islet refers to the islets of Langerhans that are present throughout the pancreas gland and mediate endocrine functions of the pancreas. These structures are also referred to herein as pancreatic islets or pancreatic beta islets. h) Beta cell refers to the beta cells that comprise beta islets. These cells synthesize and release insulin in response to physiological stimulation. i) Alpha cells refer to alpha cells that comprise the beta islets. These cells synthesize and release glucagon in response to physiological stimuli. j) Delta cells refer to delta cells that comprise the beta islets. These cells synthesize and release somatostatin in response to physiological stimuli. Other specific terms are defined herein as they are used.

The process of the present invention includes the following steps: 1) Establish a culture of mesenchymal cells, 2) Induction of cells expressing epithelial markers, 3) Isolation and cloning of cells expressing epithelial markers, 4) Maintain and expand the isolated cells, and 5) Differentiate the isolated cells into a specific cell type. The following provides a detailed description of the process of the present invention.

1. Establish a Culture of Mesenchymal Cells

The present invention includes the use of various sources of cells in establishing a culture of mesenchymal cells. For example, a mixed cell culture may be established from a primary culture of dispersed animal tissue, followed by methods to derive a mesenchymal cell culture. Primary cultures commonly contain a variety of cell types including, for example, mesenchymal, epithelial, and endothelial cells due to the composition of tissues used to establish the primary culture. Alternatively, a culture of a known mesenchymal cells (e.g., from a known mesenchymal cell line) may be established without the necessity of isolation of mesenchymal cells from other cell types in the culture. In the broadest sense, a culture of mesenchymal cells may be derived from any source of animal cells at any developmental stage or any mesenchymal cell line wherein it is possible to establish a viable culture according to methods that are well known to those skilled in the art of cell culture.

Within the context of the isolation of stem cells capable of differentiation into beta islet cells, the preferred cellular sources are: cell lines, pancreatic tissues and partially differentiated stem cells. Cell lines include, but are not limited to, the VIT1 cell line (Vitro Diagnostics, Inc. Catalog Numbers VC03007, VC03008, VC03009, VC03030, VC04033, VC04034 and VC04035), the LT2 cell line (Vitro Diagnostics, Inc. Catalog Numbers VC03004, VC03005, VC03006, and VC03029) and other suitable cell lines capable of generation of beta islet cells using the methods described herein. Pancreatic tissue includes the pancreas gland from human and animal species including canine, feline, equine, bovine, ovine, rat and mouse as the source of cells for generation of beta islets. The human pancreas gland includes adult tissue, neonatal and fetal pancreas gland of any gestational age, especially 14 to 36 weeks, more preferably 16 to 22 weeks, and most preferably 18-22 weeks. The pancreas gland of the animal species listed above also includes the use of adult, neonatal and fetal tissue. Embryonic stem cells may be used as the source of cellular material for establishment of mesenchymal cell cultures given that sufficient differentiation has occurred to generate mesenchymal cells. Partially differentiated stem cells may also be used including those that are committed to the pancreatic lineage or other partially differentiated stem cells that may be directed to differentiate into beta islet stem cells. An operational or functional characteristic of the cells used as a source for cultures of mesenchymal cells according to the present invention as applied to generation of beta islet stem/progenitor cells is that these cells may be induced to generate functional beta islet cells upon exposure to the specific environmental conditions necessary to induce such growth and differentiation (such conditions being described below).

Cell lines and stem cells include dissociated, intact cells in suspension within appropriate buffers, prepared according to commonly used methods readily apparent to those skilled in the art. Cells derived from tissues require the combined use of mechanical and enzymatic dissociation methods resulting in the generation of isolated cells and groups or clusters of associated cells containing beta islets (e.g., islet-like cell clusters ILCC). Enzymes used for dispersion include, but are not limited to, collagenase, hyaluronidase, trypsin, disbase, and Liberase. It is preferable to use mechanical disruption of the tissue through microsurgical/homogenization procedures well known in the art followed by enzymatic dispersion using collagenase at a concentration of 0.5 to 5 mg/ml, most preferably at 0.5 mg/ml, in suitable buffer such as phosphate-buffered saline either with or without added calcium, magnesium or EDTA. A most preferable embodiment involves mechanical disruption into tissue fragments that are at least 1 mm$^3$ in size followed by digestion in 0.5 mg/ml collagenase in PBS containing 1 mM EDTA, pH 7.2 to pH 7.5 at 37° C. for about 30 minutes. Other variations of this general method will be apparent to those skilled in the art and the present invention is not limited by the specific procedures used to generate dispersed tissue. Following enzymatic disruption, the enzymes used to prepare the dispersed tissue are washed out using a suitable solution such as phosphate-buffered saline followed by centrifugation by methods readily apparent to those skilled in the art.

Establishment of a mesenchymal cell culture involves use of cell culture medium for the growth of the cells. This medium is comprised of: a) base medium, b) supplements, and c) growth factors. The basal medium includes commonly used formulations well known to those skilled in the art including: RPMI, other commonly used basal media and preferably MEM or more preferably the alpha modification of MEM ($\alpha$-MEM). These basal media also contain commonly used buffers to maintain physiological pH during the cell culture process, including but not limited to, sodium bicarbonate, HEPES and other buffer substances with a pKa in the physiological pH range. Supplements added to the basal medium also include those commonly used in cell culture including transferrin or other iron-chelating agents, insulin (including natural or recombinant forms, insulin-like growth factors I & II, and related substances), trace elements, sodium pyruvate, non-essential amino acids, dextran at various molecular sizes, hydocortisone, ethanolamine, glucose and the tri-peptide, glycyl-histidine-lysine. The appropriate concentrations & compositions for such supplements will be readily apparent to those skilled in the art. Optimal levels of cell culture medium constituents are often determined through an empirical process of testing potential concentrations against a defined endpoint including for example, the growth rate of the cells, etc. The exact formulation of various basal medium supplements may be varied from the list of specific supplements described above while still retaining the specific characteristics of the present invention that primarily includes the ability to support growth of the mesenchymal cell culture.

Separation of mesenchymal cells from a mixed primary cell culture according to the present invention occurs by various methods well known to practitioners of the art of cell culture. These methods include differential adsorption, density gradient centrifugation and more preferably, selection of mesenchymal cells by use of specific cell culture conditions or most preferably, through sorting based on expression of specific cell surface markers characteristic of mesenchymal cells, for example Thy-1 or $CD_{90}$ (Saalbach, et al, 1997). Sorting of positive from negative cells occurs by well-known methods including FACS or immunomagnetic-based separation methods. Identification of mesenchymal cells is based upon morphological criteria and more importantly, the expression of specific markers of mesenchymal cells without similar expression of markers characteristic of other cells, e.g., epithelial cells. Most preferably, mesenchymal cells express $CD_{90}$ and vimentin and do not express Ep-CAM, E-Cadherin and cytokeratins including the AE1/AE3 form.

2. Induction of Cells Expressing Epithelial Markers

Following establishment of the mesenchymal cell culture according to the method described above, the present invention includes the induction of cells within the mesenchymal cell cultures that express markers of epithelial cells. In the broadest sense, these methods include those procedures well know to skilled practitioners of the art that induce epithelial marker formation in a cell population. These include exposure of the mesenchymal cell culture to growth factors or other environmental conditions resulting in epithelial marker expression. It will also be apparent that different mesenchymal cell cultures will respond differentially to various environmental manipulations that potentially may result in the expression of epithelial cell markers. The present invention is not intended to be limited by the differential requirements of specific mesenchymal cell cultures and is intended to embody all such procedures that result in the expression of epithelial markers within the previously established mesenchymal cell cultures.

According to the present invention, beta islet progenitor cells may be derived from cultures of VIT1 cells, LT2 cells, and primary cultures of pancreatic cells or stem cells that are derived, prepared and maintained in cell culture according to methods herein described. The cell lines known as VIT1, LT2 and other beta islet progenitor cell lines will not normally express epithelial markers and such expression is induced in these cells according to the following process. Epithelial marker expression is preferably induced by exposure of these cultures to members of the pituitary adenylate cyclase-activating polypeptide (PACAP)/glucagon superfamily including, but not limited to, glucagon, glucagon-like peptide-1 (GLP-1), GLP-2, glucose-dependent insulinotropic polypeptide (GIP), GH-releasing hormone (GRF), peptide histidine-methionine (PHM), PACAP, secretin, exendin-4, vasoactive intestinal polypeptide (VIP) and synthetic analogues thereof, including, but not limited to, deletions of N- or amino terminal groups. More preferably epithelial marker expression is induced by exposure to glucagon, GLP-1, and GLP-2. Most preferably the method includes induction of epithelial marker expression through use of GLP-1 or exendin-4. The concentration of GLP-1 ranges from about 2 to 15 nM, with about 10 nM being most preferable. The concentration of exendin-4 ranges from about 1 nM to 10 nM. The optimal time of exposure to these agents for the induction of insulin expression will be readily apparent to one skilled in the art. In a preferred embodiment of the present invention, exposure of cells to inducing agents for at least 4 to 6 days is necessary for induction of epithelial marker expression with a 5-day exposure being most preferred. The induction of epithelial marker expression is measured by appearance of particular marker molecules including but not limited to Ep-CAM (Epithelial Specific Antigen), E-cadherin, cytokeratins in various forms or additional markers characteristic of fully developed epithelial cells such as insulin or glucagon. Such markers can be readily identified by those of skill in the art using tools and technologies known in the art (e.g., protein or RNA detection methods).

In the context of the induction of epithelial markers in mesenchymal cultures of other, non-pancreatic tissues the inducing agents of epithelial markers also include BMP-7, fibroblast growth factor-2, lipocalin2 as well as the lipocalin superfamily, leukemia inhibitory factor (LIF), E-cadherin and transforming growth factor beta-2.

3. Isolation and Cloning of Cells Expressing Epithelial Markers

Cells expressing epithelial markers are subsequently isolated from other cells of the mixed cultures using methods well known to those skilled in the art of cell culture. These methods include, but are not limited to, selection based upon cellular expression of markers that are specific to epithelial cells. Cell surface markers specific to epithelial cells include, but are not limited to, Ep-CAM (Epithelial-Specific Antigen), E-cadherin, the cadherin superfamily, K12, K19, $CD_{44}$, EMA, CALLA, ($CD_{10}$), sialomucin, mucin, $CD_{81}$, and $CD_{166}$. Commonly used methods of cell separation include, but are not limited to, fluorescent-assisted cell sorting (FACS) or immunomagnetic separation (IMS) based on the expression of cell surface markers. In one embodiment of the methods of the present invention, the isolation of cells expressing epithelial markers through immunomagnetic separation of Ep-CAM-positive (Epithelial-Specific Antigen) cells resulted in the generation of cell lines, VIT2, VIT3 and VIT4 that are described in detail within the examples included herein.

Cell lines established by the methods described above are not necessarily clonal in nature since a variety of different cells expressing epithelial markers are typically isolated by these methods. Since it is desirable, according to the present invention, to generate clonal stem/progenitor lines as such clonal cell lines may have defined differentiation capacity (See example 5), the isolated cells expressing epithelial markers are preferably subject to additional procedures to generate clonal cell lines. In the broadest context of the present invention, cell lines clones may be established by any procedure that results in isolation of a single cell from the isolated cells expressing epithelial markers and the subsequent expansion of this single cell into a new cell line. Such methods will be readily apparent to those skilled in the art. A most preferable method of establishment of a clonal cell line is limited dilution resulting in isolation of a single cell from a mixed cell population, expansion of the single cell colony into a cell line using a growth medium and other conditions suitable for growth and expansion of the cell line.

Clonal beta islet progenitor cell lines of the present invention are derived by standard methods, including but not restricted to, limited dilution cloning or other methods that result in cell lines that are derived from a single cell. These clonal lines may be derived from primary cultures of pancreatic tissue, stem cells or beta islet progenitor cell lines including, but not limited to, VIT1 cells or derivatives including VIT2, VIT3 and VIT4 cell lines.

While the foregoing cell lines are mesenchymal in nature as described herein, there are additional embodiments of the present invention wherein cultures of mixed cellular type will naturally express epithelial markers. For example, primary cultures of the fetal human pancreas gland contain cells that express and secret insulin. Furthermore, insulin secretion is positively regulated by extracellular glucose (example 1). In addition, according to methods described in examples 4 and 5, primary cultures of the dispersed fetal human pancreas were used to establish presumptive beta islet stem cell lines that could be differentiated into cells expressing insulin and glucagon (Table III) by isolation of clonal cell lines from mixed cultures including at least mesenchymal and epithelial cells, and probably other cell types such as endothelial cells. Therefore, the present invention also includes an additional embodiment involving the isolation and establishment of clonal cell lines from cell cultures expressing epithelial markers in addition to the previously described methods involving induction of the expression of epithelial cell markers and subsequent isolation/cloning procedures.

4. Maintain and Expand Isolated Cells

Isolated cell lines expressing epithelial markers whether mixed or clonal in origin are maintained by methods readily apparent to those skilled in the art. For example, in vitro cell culture procedures as described herein may be applied to the subject cell lines and optimized as described above (See: "Establish a culture of mesenchymal cells"). Cell culture includes the use of growth medium and physical attachment/suspension culture conditions to optimize growth a given cell line. It is often necessary to engage in an empirical determination to optimize conditions necessary to ensure adequate growth of a given cell line, since many factors affecting growth are interactive and difficult to predict with certainty. The present invention is not to be limited by the exact in vitro culture conditions necessary for maintenance and expansion of a cell line expressing epithelial markers, but rather includes those conditions that result in successful maintenance and expansion of the cell lines that express epithelial markers. A preferred embodiment of the present invention includes maintenance and expansion of isolated human pancreatic cell lines using the VitroPlus II growth medium (Vitro Diagnostics, Inc. Catalog Number VC03014). Furthermore, those methods involving in-vivo expansion of subject cell lines are also embodied herein, including methods for retrieval of the cell line, such as, for example, encapsulation. The invention is not to be limited by in-vitro or in-vivo growth and maintenance of stem/progenitor cell lines but also includes, for example, ex-vivo methods that combine characteristics of both in-vitro and in-vivo environments. Cultures are contained within various suitable devices designed for cell culture, including for example, styrene tissue culture flasks, and include methods resulting attachment-dependent cultures (example 1) or alternatively, use of conditions resulting in suspension cultures. Cultures are maintained within an environment of controlled temperature, humidity, pH, gas content, e.g., $CO_2$ and may or may not include continuous circulation of oxygenated medium. In the case of static culture conditions, the medium is periodically removed and replaced with fresh medium to assure continuous cell growth within the cultures and removal of metabolites, etc. Also, these cultures are subject to periodic sub-culture by methods including, for example, enzymatic dissociation and plating into tissue culture flasks. Such methods of in-vitro cell culture and expansion are well known to those skilled in the art. The present invention is not limited to particular methods of in-vitro cell culture but broadly includes those methods that result in the growth and maintenance of stem and progenitor cell lines within an artificial environment.

A further property of cell lines isolated and maintained according to methods of the present invention is that the cell lines are immortal and self-renewing through activation of endogenous cell proliferation processes and inhibition of apoptosis. A preferred embodiment includes a mechanism of self-renewal through activation of the Wnt pathway in conjunction with activation of the hedgehog (Hh) pathway (See example 6). Such activation of these pathways occurs through processes well known to those skilled in the art including, but not limited to, activation due to presence of Wnt or Hh protein agonists and mutation of key pathway components such as ADP (Wnt) or Ptch (Hh). For example, the beta islet progenitor cell line known as VIT1 exhibits endogenous expression of the Wnt 5B gene at substantially elevated levels (example 6) that is likely to represent a mechanism of activation of the Wnt signaling pathway within VIT1 cells.

5. Differentiate the Isolated Cells into a Specific Cell Type

The isolated cells of the present invention are stem/progenitor cell lines that are capable of differentiation into any type of animal cell. In addition to the methods herein described to generate stem/progenitor cell lines, the present invention includes methods to differentiate those cell lines into terminally differentiated cell types. As will be readily apparent to those skilled in the art, there are several methods known and under current development for the differentiation of stem/progenitor cell lines into differentiated target cell types. In the broadest sense, the present invention is not to be limited by the specific methods used to induce differentiation, but rather includes use of all such methods that are operationally defined as yielding the desired differentiation into a fully differentiated cell type.

Preferably, the present invention includes methods of differentiation of stem/progenitor cell lines derived according to methods presented herein through the application of a specific growth phase sequentially followed by a specific differentiation phase. The growth phase is characterized by exposure of the subject stem/progenitor cell line to specific growth factors while the differentiation phase is characterized by a reduced rate of cellular growth under specific environmental conditions that induce differentiation. More preferably, the growth phase includes exposure of cell lines to GLP-1 (glucagon-like peptide 1), hepatocyte growth factor, beta-cellulin, growth hormone, prolactin, placental lactogen, preadipocyte factor-1, neurotrophins, activin A, activin B, gonadotropin releasing hormone (GnRH), GnRH II, Pituitary adenylate cyclase-activating peptide (PACAP), exendin-4, fibroblast growth factor (FGF), basic FGF, FGF-2, granulocyte colony-stimulating factor (G-CSF), granulocyte-macrophage colony-stimulating factor (GM-CSF), mechanical signals, (including, for example, encapsulation in fibrin and PuraMatrix™ peptide hydrogel), Wnt pathway modulation and other growth factors contained within human fetal cord serum or fetal bovine serum and parathyroid hormone. The appropriate concentrations of the various growth factors are readily apparent to those skilled in the art and may also be determined or refined by empirical variation through a suitable range of concentrations while measuring effects of such variation on appropriate endpoints. The growth medium of the present invention is intended to include both those containing serum supplementation and serum-free, animal component-free, chemically defined media. Other embodiments include specific variations of the growth medium resulting in specific enhancements of the growth and differentiation of a particular cell type within the beta islets such as alpha or beta cells.

The differentiation phase of the present invention embodies methods that result in growth arrest together with stimulation of differentiation. Since rapid cell growth often precludes differentiation (e.g., Friedman, 1976), a reduction in the rate of cell growth is necessary for cellular differentiation. Methods of cell growth reduction will be readily apparent to the skilled practitioner of cell culture and the present invention is not be limited by use of a particular method to slow growth but rather includes all such methods yielding the desired result of terminal differentiation of the stem/progenitor cell line derived according to methods described herein. A preferred method of cell growth reduction is by limited serum concentration i.e., "serum starvation" while using an otherwise fully supplemented medium to support growth. Most preferably, growth rate is slowed by employing VitroPlus II medium (Vitro Diagnostics, Inc. Catalog Number VC03014) containing 0.5% serum. Differentiation of stem cells may also involve use of specific agents to induce cellular differentiation in combination with conditions that result in slowed cellular growth. Preferably, the well known differentiation agent, nicotinamide (e.g., Mngomezulu and Kramer, 2000) is used together with reduced serum VitroPlus II to induce differentiation of human beta islet cells. The effective concentration of nicotinamide varies from 5 to 20 mM, with a preferred concentration range of 8 to 15 mM and a most preferable concentration of about 10 mM. Additional differentiation agents are also embodied within the context of the present invention including, for example, phospatidylinositol 3-kinase inhibitors (US 2002/0037276 A1; Hori, et al, 2002) mechanical signals and modulation of the expression of the Wnt pathway.

The use of a growth phase followed by differentiation requires a particular time of exposure to these conditions in order to induce terminal differentiation of stem cells. While the present invention is not to be limited in scope by variation in the time of exposure to these conditions, it is preferred that the growth phase consist of at least 4 to 6 six days in continuous cell culture (with at least 5 days being optimal) followed by at least 4 to 6 days continuous culture under differentiation conditions as described herein, with at least 5 days in differentiation conditions being optimal.

In-vitro growth and differentiation of beta islets through the process of the present invention may also involve use of extracellular matrices well known to those skilled in the art such as feeder cells, MATRIGEL® basement membrane matrix (basement membrane preparation extracted from the Engelbreth-Holm-Swarm mouse sarcoma), etc. Preferably, the extracellular matrices include, but are not limited to, PuraMatrix™ peptide hydrogel (BD Biosciences, Catalog Number 354250) and fibrin.

In addition to the methods of differentiation herein described, the present invention also includes procedures to alter or control the phenotypic properties of fully differentiated cells derived from the stem/progenitor cell generated according to the processes of the present invention. These processes involve manipulation of cellular control systems including, but not limited to, inhibition of endogenous interfering RNA that block expression of key phenotypic properties of differentiated cells. For example, the microRNA known as miR-375 which through interaction with myotrophin suppressed glucose-stimulated insulin secretion from beta cell lines (Poy, et al, 2004). The present invention also includes use of promoters that regulate gene expression of components of phenotypic expression by binding to endogenous regulatory elements. Preferably, the present invention includes use promoters that induce expression of genes involved with glucose-stimulated insulin secretion such as glucose transporter 2 (GLUT2) and glucokinase. Such promoters include hepatocyte nuclear factor 4 alpha, hepatocyte nuclear factor 1 alpha, and the homeodomain protein, pancreatic duodenum homeobox 1 (PDX-1) also known as IPF-1/STF-1/IDX-1. Also, inducers of insulin and GLUT2 gene expression such as prolactin (e.g., Sorenson and Brelje, 1997) may also be used to control the phenotype of the beta islet cells derived from progenitor cells according to the present invention. Factors that control phenotypic properties may be added directly to the medium or expressed within beta islet cells using methods of gene expression well known to those skilled in the art. While exemplified by specific agents known to regulate phenotypic expression in beta cells, those skilled in the art will recognize similar procedures that are specific to other fully differentiated cell types, and the present invention is intended to embody such manipulations of phenotypic expression.

In addition to the foregoing procedures described above with particularity for the generation of stem and progenitor cell lines and their differentiation into fully differentiated cell types, the present invention also embodies specific cell lines that are produced by the processes herein described. The present invention includes the following cell lines: VIT1, LT2, VIT2, VIT3, VIT4 and VIT5 and any derivative thereof. The cell lines also include the following specific clonal cell line derivatives of the VIT2, VIT3, VIT4 and VIT5 cell lines: VIT2-A2, VIT2-A11, VIT2-B4, VIT2-C12, VIT2-G1, VIT2-G6, VIT2-H9, VIT3-B4, VIT3-C8, VIT3-F1, VIT3-F4, VIT3-F7, VIT3-G12, VIT3-H11, VIT4-C4, VIT4-D10, VIT4-F9, VIT4-G9, VIT4-H9, VIT5-D12, VIT5-H2, VIT5-H9, VIT5-H12. These cell lines are described in example 5. Most preferably, the present invention includes the clonal cell line known as VIT4-G9 and VIT3-G12.

The human pancreatic cell line, VIT 1, was deposited with the American Type Culture Collection (ATCC), 10801 University Boulevard, Manassas, Va. 20110-2209 USA, on Oct. 16, 2007, under the terms of the Budapest Treaty On The International Recognition Of The Deposit Of Microorganisms For The Purposes Of Patent Procedure, and was assigned ATCC Accession No. PTA-8686.

The human pancreatic cell line, VIT4-G9, was deposited with the American Type Culture Collection (ATCC), 10801 University Boulevard, Manassas, Va. 20110-2209 USA, on Oct. 10, 2007, under the terms of the Budapest Treaty On The International Recognition Of The Deposit Of Microorganisms For The Purposes Of Patent Procedure, and was assigned ATCC Accession No. PTA-8683.

Another embodiment of the present invention includes any cell line derived according to the processes of the invention. A further embodiment includes progenitor cell lines that give rise to specific cells of the beta islet such as the alpha cell, beta cell, delta cell or polypeptide-producing cell (PP cell). Thus, for example, clonal derivatives of the VIT2 cell line, e.g., VIT2-A11 may selectively give rise to beta cells of beta islets (Example 5). Another embodiment of the present invention also includes progenitor cells that give rise to multiple cell constituents of beta islets at the exclusion of particular cell types, e.g., beta islets containing alpha and beta cells but lacking delta and polypeptide-producing cells.

In addition to the processes and cell lines described herein, the present invention also embodies various applications of the stem and progenitor cell lines and fully differentiated cells arising there from. In the broadest context, the uses of the present invention are intended to be all-inclusive and not limited to particular applications. Preferably, the present invention is intended for broad uses in medical research, testing, toxicology, product development and additional therapeutic applications involving, in a broad context, the area of cellular therapy without limitation to animal species, specific type of fully differentiated cell type, or method of transplantation of cells. As used herein, cell therapy is intended to include any therapeutic application derived from use of the stem cells or the derivative terminally differentiated cell types derived from use of the methods herein described. Furthermore, additional medical devices are also embodiments of the present invention, including, but not limited to, cell culture media and systems designed to support growth, maintenance and differentiation of the cell lines derived through the processes of the present invention.

Cell therapy utilizing processes and products of the present invention is exemplified, but not limited by, application to the treatment of diabetes, including type I diabetes mellitus and type II diabetes mellitus, through use of beta islet stem cell lines or fully differentiated beta islet cells produced through the methods described herein. In-vivo growth and differentiation of beta islets may result from transplantation of beta islet cells or beta islet stem cells, e.g., VIT4-G9 cells, produced according to methods herein described, or stimulation of beta islet growth and differentiation from endogenous beta islet stem/progenitor cells. Intraportal transplantation of purified beta islets has been previously described and includes use of adjuvant therapy to block immune rejection of beta islets when these transplants occur into animals or humans with type I diabetes mellitus. Anti-rejection therapy is necessary to prevent rejection of transplanted islets since the immune system of recipients reacts to and rejects islet cells, especially beta cells. Such anti-rejection medications include: sirolimus, tacrolimus and daclizumab (Shapiro, et al, 2000; Ryan, et al, 2001). Another method known to eliminate the immune rejection of beta islets is the encapsulation of beta islets or beta islet stem cells within structures that physically block autoimmune responses that result in the elimination of beta islets or beta cells while also allowing hormone secretion and control through permeability properties of the encapsulation device. Also embodied within the present invention is the use of stem cells, progenitor cells or fully differentiated beta islet cells derived from these cells that are immuno-privileged, or otherwise made to be immuno-privileged and thereby not rejected by recipient hosts. When beta islet cells derived according to the present invention are transplanted into a diabetic recipient, the present invention includes anti-rejection therapy, encapsulation methods or other procedures that block autoimmune destruction of beta islets. Specific agents that result in regeneration of beta islets from endogenous stem cells include GLP-1, exendin-4, HGF, and other factors that specifically induce beta islet regeneration or their derivatives that maintain capability to induce beta islet cell regeneration. In the case of the induction of beta islet regeneration from beta islet stem cells within diabetic patients, prevention of autoimmune rejection involves adjuvant anti-rejection therapy rather than encapsulation which is only suitable for transplantation methods of introducing beta islets and or stem cells into an intact organism.

While applications of the present invention focusing on treatment of diabetes by stem cell therapy are a potentially valuable use of the invention described herein, the present invention is not limited to stem cells that may be induced to differentiate into functional beta islet cells. The novel process of generating and differentiating stem cells described herein has much broader application to cell therapy, medical research and testing as will be apparent to those skilled in the art.

EXAMPLES

Example 1

Primary Cultures of Human Pancreatic Cells

These initial experiments were undertaken to establish conditions of in vitro cell culture that result in growth and differentiation of human beta islets. These results then led to additional refinements, described in subsequent examples that led to development of a new method for the generation of human beta islet stem cells.

Figure 3C:
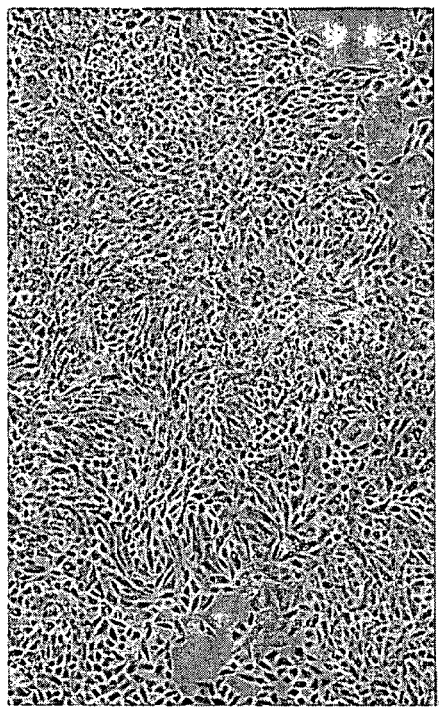
FIGS. 3A-3D show phase contrast micrographs of VIT2 and VIT3 cells at 100×.
Figure 3D:
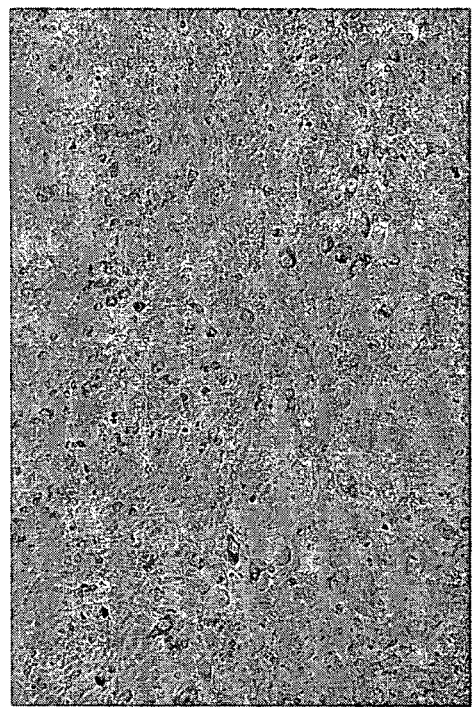
Figure 3A:
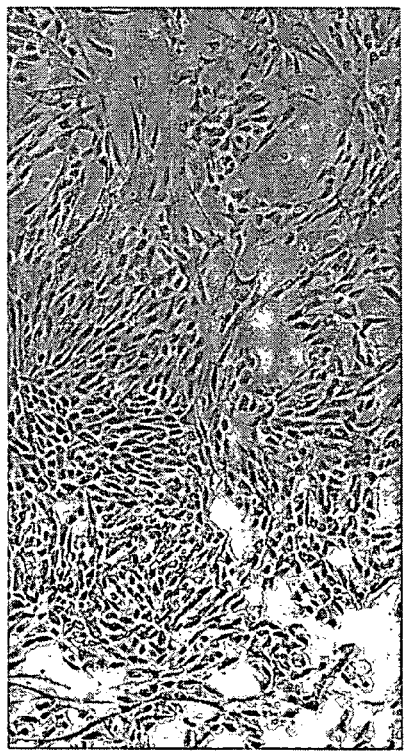
Figure 3B:
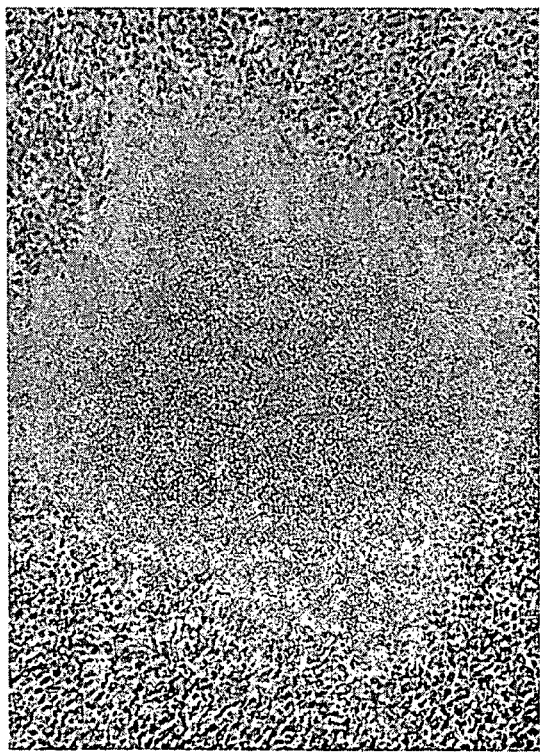

Initial studies performed on dispersed human fetal pancreas tissue indicated the importance of mechanical disruption of the tissue into approximate 1-mm$^3$ pieces followed by collagenase digestion at relatively low concentration for the successful generation of viable, in vitro beta islets. Higher collagenase concentrations and/or the disruption of tissue into smaller fragments were both found to be less advantageous to the growth and differentiation of beta islets. The following procedure was found to be effective in the establishment of proliferating cultures of human beta islets, referred to herein as islet-like cell clusters (ILCC) (McEvoy, R C, et al, 1986). ILCC are clusters of spherical, beta islet hormone-containing epithelial cells that aggregate on the surface of attached monolayer cells (See FIG. 3B, for example).

A human fetal pancreas gland at 18 weeks gestation was obtained from Advanced Biosciences Resources (Alameda, Calif.), according to NIH guidelines, and 45 CFR46 including informed consent. It was maintained in MEM, alpha modification (α-MEM; Sigma Chemical Co, Catalog Number M-0644) that also contained 10 mM HEPES, pH 7.2, 200 units/ml penicillin and 200 μg/ml streptomycin at 4° C. for 24 hours following removal and prior the procedures described below. The tissue was briefly washed in 20 mls α-MEM and then micro-dissected into pieces >/=1 mm$^3$ in a digestion medium containing RPMI 1640, 25 mM HEPES, (pH 7.2) 2 mg/ml BSA, 0.5 mg/ml Type XI collagenase (Sigma Chemical Co, Catalog Number C-9407), 100 units/ml penicillin and 100 μg/ml streptomycin. The mixture was then incubated for 30 minutes at 37° C. at 200 RPM and the collagenase digestion was stopped by the addition of 10 ml of phosphate-buffered saline (PBS; 0.1 M phosphate buffer, 0.9 M NaCl, pH 7.4, Fisher Biotech, Catalog Number BP665-1) and the mixture was centrifuged at 470×g for 10 minutes.

The supernatant was discarded and the pellet was resuspended in about 1 ml PBS and about 10 mls PBS was added. The mixture was agitated gently in a 15-ml centrifuge tube and the heavier materials including cell aggregates, ILCC, etc were allowed to settle to the bottom of the tube and the fluid above was removed by aspiration and saved by cryopreservation in α-MEM containing 10% FBS & 7.5% ethylene glycol. This process of purification was repeated three times. The sample, containing the heavier materials was a mixture of ILCC, other cellular aggregates and single cells was then centrifuged and resuspended in 1 ml MEM (Sigma, Catalog Number M-3024), containing 2 mM glutamine.

The single cell content was determined by counting with a hemacytometer (1/10 dilution) and the sample was plated at 10,000 cells/cm$^2$ in six-well cell culture plates (Corning, Catalog Number 3516 or Falcon Primaria™, Catalog Number 353846). The medium used for culture was VitroPlus II (Vitro Diagnostics, Inc, Catalog Number VC 03014), containing 5% fetal bovine serum (FBS) (Hyclone Laboratories, Catalog Number SH30071.03) and 10 nM GLP-1 (1-37) (Bachem, Catalog Number H-5552). Cultures were maintained at 37° C. within a humidified incubator maintained at 5% CO$_2$ (Forma Scientific, Inc., Model Number 3154). These cultures were periodically monitored for growth using an inverted microscope equipped with phase contrast optics (Nikon Diaphot 300). Cultures were fed every 2 to 4 days by washing the attached cells and cell aggregates 2-3 times with PBS and then adding fresh growth medium (3-4 mls per well).

As the attached fibroblast monolayer reached confluence, the cultures were sub-cultured as follows: The plates were washed twice with PBS and the number of ILCC was visually determined. A sterile-filtered dispersion medium consisting of 0.5 mg/ml Type XI collagenase (Sigma Chemical Co, Catalog Number C-9407) in 1 mM EDTA-PBS, pH 7.5, 2 mg/ml BSA, 100 units/ml penicillin and 100 μg/ml streptomycin was used to dissociate attached cells and associated ILCC. One to two ml was added per well and incubated at 37° C. for 20 minutes. The dispersed cells and ILCC were recovered by repetitive pipeting and washout with PBS (2 mls per well, twice). This mixture was centrifuged at 470×g for 10 minutes and the pellet was resuspended in 1 ml PBS and 10 ml PBS was added. The mixture was agitated gently in a 15-ml centrifuge tube and the heavier materials including ILCC, etc were allowed to settle to the bottom of the tube and the fluid above was removed by aspiration. This process was repeated twice and the fraction containing the heavier materials was centrifuged and resuspended in 1 ml MEM. It was then cultured in growth medium (VitroPlus II, 5% FBS and 10 nM GLP-1) at about 20 to 30 ILCC per well in 6-well cell culture plates (Greiner Bio-Once, Cell Star®, Catalog Number 657 160). Cultures were maintained at 37° C. within a humidified incubator maintained at 5% CO$_2$ (Forma Scientific, Inc., model number 3154). These cultures were periodically monitored for growth using an inverted microscope (Nikon Diaphot 300) equipped with phase contrast optics. Cultures were fed every 2 to 4 days by washing the attached cells and cell aggregates 2-3 times with PBS and then adding fresh growth medium (3-4 mls per well in six-well plates).

ILCC and dispersed human pancreatic cells were examined for insulin content by initial fixation in 1% glutaraldehyde (Sigma Chemical Co, Catalog Number G-5882) in 0.1 M phosphate buffer, pH 7.4, using end-over-end agitation at 10 RPM at room temperature for 60 minutes. Following centrifugation at 470×g for 10 minutes, the supernatant was discarded and fixative was washed out using 2.5 mls 2% FBS in PBS followed by centrifugation (470×g for 10 minutes). Cells were permeabilized by incubation in 0.2% Tween 20 (Sigma, catalog number P-9416) in PBS for 15 minutes at 37° C. Following centrifugation (470×g for 10 minutes) and discarding of the supernatant, non-specific binding was blocked by room temperature incubation in 5% goat serum (Jackson ImmunoResearch Laboratories, Inc, Catalog Number 005-000-121) in PBS for 30 minutes. Cells or ILCC were centrifuged (470×g for 10 minutes), the supernatant was discarded and 5 mls of primary antibody monoclonal anti-human insulin (Sigma Chemical Co, Catalog Number 12018) at 1/1000 dilution in PBS was added. Cells and ILCC were incubated in primary antibody overnight at room temperature using end-over-end agitation at 10 RPM. Cells and ILCC were centrifuged (470×g for 10 minutes), the supernatant discarded and resuspended in 0.2% Tween-20-PBS. Following centrifugation as above, the pelleted cells & ILCC were incubated in secondary antibody, goat-anti-mouse-HRP (Jackson ImmunoResearch Laboratories, Inc., Catalog Number 115-035-062) at 37° C. for 30 minutes at 150 RPM. The secondary antibody was washed out by resuspension in 5 mls PBS followed by centrifugation. Cells/ILCC were then incubated for 15 minutes in diaminobenzidine (Sigma Chemical Co, Catalog Number D-4293), centrifuged and resuspended in 100 μl PBS for microscopic examination and photography. ILCC were also examined following staining with dithizone (DTZ) according to Shiroi, A, et al., (2002). DTZ is a zinc-chelating agent that selectively stains pancreatic beta cells because of their high zinc content.

The effects of hepatocyte growth factor (HGF; PeproTech, Inc. Catalog Number 100-39) were determined by addition to the growth medium described above at a final concentration of 30 ng/ml. Others have shown that HGF induces proliferation of beta cells with the beta islets (Gracia-Ocana, et. al, 2000) and preliminary experiments suggested that ILCC growth was affected by HGF addition. The acute effects of HGF on ILCC growth and morphology were determined and longer-term experiments were conducted as follows. The sample consisted of a cryopreserved, non-settled fraction of cells resulting from sub-culture of ILCC from the first passage of the culture of human pancreatic dispersed cells prepared as described above. The frozen cells were rapidly thawed, cryopreservative was washed out and the cells were plated at 10,000/cm$^2$ during the second passage. Cultures were exposed to 30 ng/ml HGF or control medium without added HGF and the cultures were expanded through 4 passages. Thereafter, both the control and HGF cultures were maintained and expanded through 8 passages using growth medium without added HGF. The number of ILCC in these cultures was determined by microscopic inspection.

ILCC were examined to determine the level of insulin content and its secretion by use an immunoassay specific to human insulin (Linco Research, Catalog Number EZHI-14K). Since the growth medium contains recombinant human insulin, tissues were extensively washed with PBS prior to determination of secretion. ILCC were acutely maintained in a physiological saline solution (140 mM NaCl, 5 mM KCl, 5 mM CaCl$_2$, 0.5% BSA, 1 mM sodium pyruvate, 2 mM glucose, and 10 mM HEPES, pH 7.4). Insulin secretion was determined during the exposure of 50 ILCC in 2 mls of physiological saline during three successive 1-hour incubations at 37° C. in a shaker bath at 200 RPM under control conditions, elevated glucose and elevated K$^+$, respectively. The control solution contained 2 mM glucose, the elevated glucose solution was identical but contained 20 mM glucose, and the elevated K$^+$ solution contained 50 mM K$^+$, while the other constituents were identical to the control solution. The physiological saline solution was collected following centrifugation (10 minutes at 470×g) and frozen at −20° C. for later analysis. The remaining ILCC were lyzed in 10 mM Tris, 1 mM EDTA and 10% glycerol; the pellet was extracted overnight at 4° C. in 70% ethanol, 0.18 mM HCl and the extract was dried using Model DNA 110 Speed Vac (Savant, Inc.). The dried extract was reconstituted in 100 µl PBS prior to assay for insulin content.

Within the first 24-hours of establishing primary culture of dispersed human pancreatic cells, fibroblast-like and epithelial-like cells attached to culture plates and formed monolayer clusters of cells, together with isolated cells. Also, ILCC were commonly observed and these were typically associated with fibroblast-like colonies. These structures consisted of several spherical cells clustered together on top of the underlying fibroblast monolayer. These ILCC were maintained and proliferated in cell culture. ILCC appeared to be derived from the fibroblast-like monolayer cells. ILCC were sometimes found in close proximity to each other, rather than randomly distributed throughout the culture, possibly indicating the involvement of soluble factors elaborated by ILCC in the induction of ILCC growth from these cultures. In the earlier stages of growth, the underlying fibroblast monolayer continually expanded eventually becoming confluent. During this time, ILCC did not appear to expand in size.

Increase in islet size, was apparent after longer periods of culture. The underlying fibroblast monolayer expanded to become confluent at 7 days while the ILCC maintained a similar diameter. However, at 12 days, the ILCC expanded considerably in diameter (data not shown). Growth of ILCC in these cultures was also apparent by an increase in the number of ILCC. Analytical procedures demonstrated the presence of insulin within these ILCC suggesting that the ILCC contain beta cells. The DAB stain in ILCC that were fixed and reacted with an insulin-specific monoclonal antibody (MAB) was localized primarily in peripheral regions of the ILCC with some regions staining more intensely than others (not shown). The IHC procedure also stained about 20% of the individual cells in dissociated cell preparations of human pancreatic tissue (not shown). The presence of insulin within ILCC is corroborated by evidence showing positive staining for dithizone (DTZ), a zinc-chelating stain that is also known to indicate beta cells, since insulin complexes specifically with zinc within beta cells (Shiroi, et. al., 2002). Also, analysis of ILCC extracts by immunoassay specific for human insulin, revealed significant insulin levels within ILCC. The insulin content within the extracts was about 2.5 µU (n=4) or about 50 nU insulin/ILCC. Since ILCC showed positive reactions to staining by an insulin-specific MAB and DTZ, and also contained extractable human insulin, it is highly likely that these ILCC contain beta cells that are known components of human beta islets. A further property of beta islets is the ability to secrete insulin in response to elevated glucose concentration and ILCC derived from the above cultures were tested for glucose-stimulated insulin secretion by methods described above. Basal secretion of insulin could be measured from ILCC under control conditions, 2 mM glucose, and this secretion was increased by exposure to 20 mM glucose. Also, insulin secretion was induced by exposure of a population of fibroblast-like cells from which the ILCC were derived to 20 mM glucose and exposure of these cells to 50 mM K$^+$ also induced increased insulin release. These results together with the previous results showing that ILCC contain insulin also indicate that the ILCC contain human beta cells since exposure to elevated glucose resulted in increased insulin secretion.

To determine if ILCC cultures were affected by environmental conditions, the effect of HGF exposure was determined as described above (See: Methods). HGF is known to be mitogenic to beta cells, increases beta cell mass and total insulin production in vivo (Gracia-Ocana, et. al, 2000). HGF is also a known survival factor for a variety of cells (Dai, et. al, 2003). Exposure of primary cultures of dispersed human pancreatic cells to HGF had both acute effects and a longer-term, more chronic effect. Within a short time of exposure, 30 ng/ml HGF resulted in a shift in the morphology of ILCC from larger islets containing small cells to more loosely attached, smaller islets composed of larger cells. This effect on islet morphology was reversed within a few passages, when HGF was removed from the culture medium. Also, a longer-term effect was observed resulting in a significant increase in the number of ILCC within cultures previously exposed to HGF. At the early stages of pass 7, following continuous exposure to HGF during passages 2 through 4, the number of ILCC increased by nearly 5-fold while there was no similar increase in ILCC number within untreated cultures (data not shown). It is thus apparent that ILCC cultured as described herein are influenced by environmental factors, probably involving both differentiation and proliferation effects.

Methods are described resulting in the establishment of apparently functional human beta islets in primary cultures of dispersed human fetal pancreatic cells. These islets are maintained for up to four months using the described procedures of in vitro cell culture.

Example 2

Establishment and Characteristics of Human Pancreatic Mesenchymal Cell Lines The results described in example 1 suggest that beta islets may be derived from mesenchymal cells in primary culture. On the other hand, studies of the proliferative capacity of beta islets maintained in in-vitro cell culture indicate that islets do not proliferate and rapidly lose functional properties including insulin content and its secretion in response to elevated glucose (McEvoy, et. al, 1986). In this example, various methods were used to establish purified cultures of mesenchymal cells from dispersed cells derived from the human fetal pancreas. The methods for generation of these cell lines are described together with some of the basic characteristics of these cell lines.

The cell line known as VIT1 arose from a primary culture of dispersed human fetal pancreatic cells under conditions that select for growth of fibroblast cells. A single pancreas gland at 18 weeks gestation (Advanced Biosciences Resources; Alameda, Calif.) was dispersed by micro-dissection and collagenase digestion (2 mg/ml for 50 minutes at 37° C.). Following washout of enzyme, cells were frozen down at about 1° C./minute in α-MEM, 10% FBS & 7.5% ethylene glycol and stored in liquid $N_2$. Frozen cells were subsequently rapidly thawed at 37° C., washed with 10 mls PBS and plated at a low density (~200/$cm^2$), favoring the selection of fibroblasts, in VitroPlus II growth medium (Vitro Diagnostics, Inc, Catalog Number VC03014).

Another cell line, known as LT2 arose by purifying mesenchymal cells from a primary culture of dispersed human fetal pancreatic cells. A single pancreas gland at 18 weeks gestation (Advanced Biosciences Resources; Alameda, Calif.) was dispersed by micro-dissection and collagenase digestion (2 mg/ml for 50 minutes at 37° C.). Following washout of enzyme, dispersed cells were incubated with magnetic beads coupled to anti-mouse IgG monoclonal antibodies though a DNA linkage (Dynal Biotech, Catalog Number 115.31) that had previously been coupled to a murine monoclonal antibody to Thy-1, referred to herein as $CD_{90}$ (Dianova, Catalog Number Dia 100) according to the manufacturer's suggested procedure. Magnetic isolation and the detachment of the magnetic beads by DNAse treatment resulted in the separation of fibroblasts from epithelial cells (Saalbach, et al, 1997) and establishment a primary culture of human pancreatic mesenchymal cells. The $CD_{90}$ positive cells were then cultured in VitroPlus II (Vitro Diagnostics, Inc., Catalog Number VC03014) growth medium and transfected with an expression vector containing the large T antigen sequence. Antibiotic selection was used to select transfectants that became the LT2 cell line. Cultured cells were visualized using an inverted, phase contrast microscope (Diaphot 300, Nikon).

Cell Growth Analysis: Cell lines were expanded using the optimized growth medium, VitroPlus II. Cell culture media was prepared according to the package insert for these products. Briefly, the basal medium, alpha-MEM (Vitro Diagnostics, Inc; Catalog Number VC03015) was prepared by reconstitution using water for injection (Vitro Diagnostics, Inc; Catalog No. VC03016) and sodium bicarbonate (Sigma Chemical Co; Catalog No. S-5761) was added to 2.2 gm/Lt. Base medium was stored in a vented T-75 flask within a 5% $CO_2$ tissue culture incubator at 37° C. As needed, complete medium was prepared by addition of the appropriate volume of concentrated supplement (Vitro Diagnostics, In; Catalog Number VC03014) to the base medium just prior to use. The VIT1 and LT2 cell lines were grown to approximate confluence, digested with Accutase™ (Innovative Cell Technologies, Inc, Catalog Number AT104) for 15 minutes at 37° C. and sub-cultured at about 5,000 cells/$cm^2$ in VitroPlus II growth medium using T-25 flasks (Corning). Cells were washed with PBS (×3) and fresh growth medium was added every 3 to 4 days. Doubling time ($t_d$) was calculated as $(\ln(2) \Delta t/\ln(c_f)/(c_i))$ where $\Delta t$ is time in hours between plating and sub-culture, $c_i$ is the number of cells plated and $c_f$ is the number of cells at the time of sub-culture as determined by a hemacytomer or automated cell counter. The number of population doublings during a passage was calculated as $\Delta t/t_d$ and the total population doublings was the sum of the population doublings in all passages.

Immunohistochemistry: Cells were grown to 60 to 70% confluence in 24-well plates using growth medium, washed with PBS and fixed in 70% MeOH-30% acetone at −20° C. for 30 seconds followed by 3 washes with PBS. Non-specific binding was blocked by incubation with 5% goat serum (Jackson ImmunoResearch, Inc; Catalog number 005-000-121) in PBS for 30 mins, followed by 3 washes with PBS. Various primary antibodies were prepared in PBS at 2-5 µg/ml and reacted with cells for 30 minutes at room temperature followed by 3× washout with PBS and incubation with secondary antibody, HRP-conjugated goat anti-mouse IgG (Jackson Laboratories, Inc., Catalog Number 115-035-062) at 2 µg/ml for 20 minutes at room temperature and 3 washes with PBS. Primary antibodies used for immunohistochemistry were: Vimentin: Clone V-9, Sigma Chemical Co, Catalog Number V6630 or Santa Cruz Biotechnology, Catalog Number AC-6260; $CD_{90}$: Dianova, Catalog Number DIA100; Ep-CAM: Biogenesis, Catalog Number. 4240-4009; E-Cadherin: Sigma Chemical Co. Catalog Number C-1821; Cytokeratin AE1/AE3: Dako, Catalog Number M3515. Peroxidase was detected by reaction with Sigma Fast Diaminobenzidine (Sigma Chemical Co.) according to the manufacturer's procedure. A negative result showed no positive (brown) cells whereas a positive result was reported when about 5% or more of the total cellular population were positive.

Figure 1A:
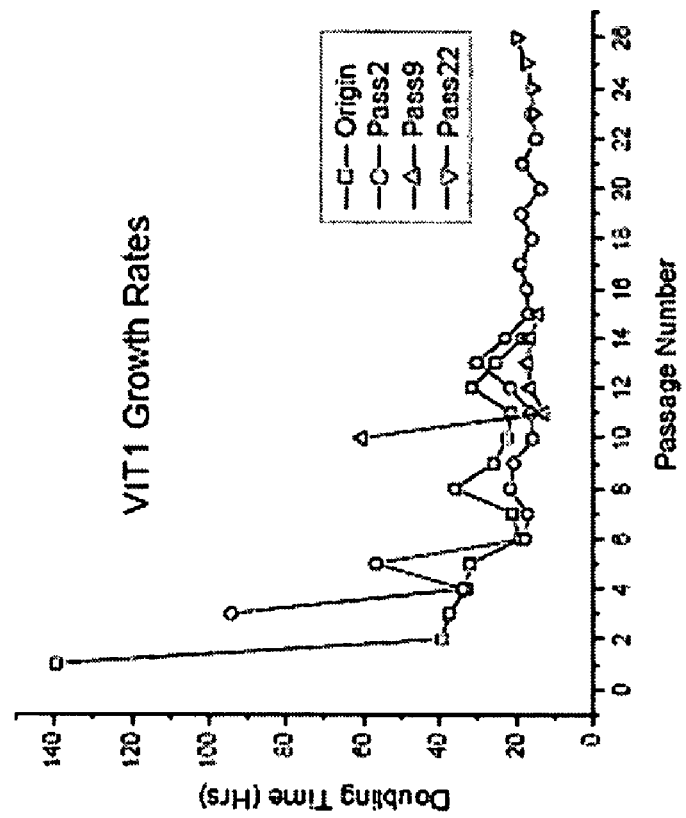

VIT1 cells grew at an intermediate rate (doubling time ($t_d$) about 30 hours) during the initial 6 passages followed by more rapid growth ($t_d$~20 hours) through approximately 130 population doublings (26 passages) as shown in FIG. 1. VIT1 cells exhibited a classic fibroblastic morphology during its initial six passages, while after pass 6 when the growth rate increased, there was also a change in morphology to epithelioid. (The minor increases in growth rates seen at passes 8, 12 and 13 were not reproducibly observed and are thus not likely to be characteristic of the cell line.) Also, there were no indications of growth rate changes at later passages. VIT1 cells are diploid since a single $G_0$-$G_1$ peak was detected by flow cytometry cell cycle DNA analysis. Furthermore, VIT1 cells from early and later passages were both diploid indicating an absence of ploidy change during the transition from slower to more rapid growth rate. VIT1 cells express the mesenchymal markers vimentin and $CD_{90}$ but not common markers of epithelial cells (Table 1).

After an initial adaptation at lower passages, the mesenchymal cell line LT2 grew rapidly with a doubling time of 15-25 hours that was maintained through about 200 population doublings (40 passages) as shown in FIG. 1, without indication of significant or sustained growth rate change. LT2 cells are diploid as revealed by DNA cell cycle analysis and express markers of mesenchymal cells but do not express epithelial markers (Table 1). Since large T antigen is expressed and these cells have been expanded through ~200 population doublings, it is likely that large T antigen is involved with the prolonged proliferative capability of the cell line. However, it is also possible that other mechanisms are involved with prolonged proliferation, since cells expressing large T antigen rarely circumvent secondary senescence possibly because of telomere shortening due to a lack of telomerase activity (Montalto, et al, 1999; Stein, 1985). Most human fibroblasts expressing large T antigen undergo senescence at about 70 to 80 population doublings (20-30 doublings beyond replicative senescence) due to crisis and an inability to survive secondary senescence (Macera-Bloch, et al, 2002). Since LT2 cells have been expanded through 200 population doublings, additional mechanisms of long-term proliferation of human pancreatic mesenchymal cells are likely and this issue investigated further and discussed in example 6, below.

TABLE I

Immunohistochemistry Analysis of Human Pancreatic Cells

| Cell Line/ passage | Vimentin | CD 90 | Ep-CAM | E- Cadherin | Cytokertin AE1/AE3 |
|---|---|---|---|---|---|
| LT2 Ps 7 | + | + | − | − | − |
| VIT1 Ps 5 &7 | + | + | − | − | − |
| Pancreatic primary | + | + | + | + | + |

Procedures are described that result in cultures of human pancreatic mesenchymal cells by use of methods to select or purify fibroblast cells from preparations of mixed cells derived from human fetal pancreatic cells. The mesenchymal cell lines VIT1 and LT2 exhibit classic markers of mesenchymal cells including vimentin and $CD_{90}$ while not expressing the epithelial markers Ep-CAM, E-cadherin or Cytokeratins AE1/AE3 and show characteristic morphology of fibroblasts at the earlier passages, providing evidence of their mesenchymal nature. The VIT1 cell line exhibits a maintained doubling time of about 17 hours from passage 15 to 26, through approximately 130 population doublings. Since mortal human fetal cell lines have the capacity to double only about 50 times (Hayflick, 1985), the maintained expansion of the VIT1 cell line through 130 populations indicates apparent immortality, even though this cell line was not transfected with a gene, e.g., large T antigen, known to result in extended proliferative capability. Thus, the VIT1 cell line was further investigated as a potential self-renewable source of stem cells capable of generating human beta islets.

Example 3

Induction of Epithelial Cells in Cultures of Human Pancreatic Mesenchymal Cells

Initial experiments showed that when VIT1 cells are cultured under conditions that induce the growth and differentiation of beta islets from primary cultures of dispersed human pancreatic cells as described above (example 1), this also results in the growth and differentiation of ILCC that were shown to contain insulin suggesting that the ILCC derived from VIT1 cells contain beta cells which are known to be epithelial cells. This example describes these results in greater detail and defines conditions that induce the formation of epithelial cells from the VIT1 mesenchymal cell line.

VIT1 cells were cultured and expanded through multiple passages as described in Example 2, "Cell Growth Analysis". The culture medium used for expansion was VitroPlus II, (Vitro Diagnostics, Inc, Catalog Number VC03014) containing 10 nM GLP-1 (1-37) (Bachem, Catalog Number H-5552). Different cultures were expanded for 11 to 20 days encompassing two to five passages prior to immunohistochemical determination of insulin or Ep-CAM. A negative control culture that was expanded in VitroPlus II without added GLP-1 through 6 passages (24 days) prior to IHC determination of insulin. Insulin and Ep-CAM presence within these cultures was determined by fixation of the cultured cells in 1% glutaraldehyde, overnight incubation with insulin MAB (Sigma Chemical Co, Catalog Number I2018) at 1/1000 dilution in PBS or Ep-CAM, (Epithelial Specific Antigen) MAB (Biogenesis, Catalog Number 4240-4009) at 1/200 dilution in PBS followed by washout and incubation with an HRP-conjugated secondary antibody (Goat-anti-mouse-HRP (Jackson ImmunoResearch Laboratories, Inc., Catalog Number 115-035-062) at 37° C. for 30 minutes. Following washout of the secondary antibody, the fixed cells were then incubated for 15 minutes in diaminobenzidine (Sigma Chemical Co, Catalog Number D-4293), and the stained cultures were examined by phase-contrast microscopy and photographed.

An initial experiment begun at the $4^{th}$ passage showed the appearance of small ILCC as the culture reached confluence and the frequency of ILCC expanded considerably during the fifth passage after about 2 weeks culture in GLP-1-containing growth medium. These ILCC were also shown to contain insulin by IHC while the underlying VIT1 cells that give rise to ILCC were generally non-reactive. Nearly all of the ILCC were positive for insulin and the percentage of insulin positive cells within a given ILCC ranged from about 5 to 60% (Data not shown). These results were repeated in a total of 3 independent determinations using VIT1 cells at passage 5 (twice) or 12. Ep-CAM (Epithelial Specific Antigen) was also induced in these cultures and appeared to have a similar distribution as insulin. However, ILCC profiles were greatly reduced in frequency (about a thousand-fold) within the negative control culture lacking GLP-1 in the medium and these ILCC were generally negative for insulin although insulin positive ILCC were rarely observed. Also, VIT1 cells that were not exposed to GLP-1 were negative for Ep-CAM as described in example 2 (above).

The human pancreatic mesenchymal cell line, VIT1, may be induced to form epithelial cells including islet-like cell clusters that contain human insulin and cells that express the epithelial-specific marker, Ep-CAM, when exposed to GLP-1 as described herein. This may result from the existence of stem cells within the human pancreas that possess properties of mesenchymal cells including fibroblast morphology and expression of mesenchymal markers that are capable of differentiation to beta islet cells when exposed to appropriate environmental signals. The derivation of epithelial cells from mesenchymal is unexpected according to classic developmental biology paradigms and known developmental processes that underlie development of the pancreas gland and beta islets (Edlund, 2001 & Jensen, 2004).

Example 4

Generation of Human Beta Islet Progenitor Cell Lines

The previous results presented in examples 1 and 2 shows that mesenchymal cell lines, e.g., VIT1 or LT2, are derived from dispersed human fetal pancreas cells. When these cells are exposed to physiological concentrations of GLP-1, an agent known to promote proliferation and development of beta cells (Doyle and Egan, 2001), epithelial cells were induced including ILCC that contain insulin. It thus appeared possible to isolate cellular components of human beta islets from VIT1 cells induced to express insulin through a strategy involving separation of Ep-CAM expressing cells since alpha, beta and delta cells are epithelial and these may subsequently be isolated from mixed epithelial cultures by cellular cloning. In this example, procedures are described for the isolation and cloning of cells expressing an epithelial cell marker, Ep-CAM, from the mesenchymal cell line, VIT1.

Cell lines known as VIT2, VIT3 and VIT4 were established from cultures of VIT1 cells as follows. VIT1 cultures were established from frozen stocks and expanded in VitroPlus II (Vitro Diagnostics, Inc, Catalog Number VC03014) containing 10 nM GLP-1, referred to as VitroPlus II/GLP-1, for a sufficient amount of time to induce insulin & Ep-CAM positive cells, as determined by immunohistochemical analysis described in example 3, above. Some of the cell lines were also exposed to 10 mM nicotinamide to promote differentiation of beta cells although 5-day exposure to nicotinamide did not appear to change the number of insulin or Ep-CAM positive cells in VIT1 culture by IHC analysis (Data not shown). Cultures of 10 to 20 million cells consisting of attached cell monolayers and associated ILCC were dissociated by Accutase™ (Innovative Cell Technologies, Inc, Catalog Number AT104) digestion (15 minutes at 37° C.), washed with PBS and bound to magnetic beads conjugated to a monoclonal antibody directed to Ep-CAM (Ber-EP4) specific to 34K and 39K antigens expressed on epithelial cells. Binding reactions occurred at 2.5 million cells/ml containing 4 beads (CELLection™ Epithelial Enrich; Dynal Biotech Catalog Number 162.01) per cell in 0.1% BSA-PBS at room temperature with 10 RPM end-over-end rotation for 60 minutes (Dynal Stirrer, Model 10102). Non-bound cells were separated from bound by magnetic attraction of bound cells and washout with 0.1% BSA-PBS (3 mls, four repetitions). Magnetic beads were then removed from cells by DNase digestion according to the manufacturers' procedure. The recovered cells were cultured to 80 to 90% confluence in single wells of 48-well plates (Falcon, catalog number 353078) using VitroPlus II/10 nM GLP-1 as growth medium.

The VIT5 cell line was established as follows. A primary culture of human fetal pancreatic cells was established as previously described (example 1). A sample containing ILCC from passages 5 & 7 was sub-cultured at about 1.5 ILCC per cm² and cultured for 3 months without sub-culture. The number of ILCC remained low and relatively constant (about 8 ILCC in the entire culture) through about 48 days and thereafter increased rapidly following routine feedings (~ every 10 days) up to 106 ILCC. After 3 months continuous culture, disperse ILCC were prevalent consisting of a few cell layers on top of monolayer fibroblast-like cells approximately 0.6 to 1.0 mm in diameter. This culture was dispersed by collagenase digestion (0.5 mg/ml in 1 mM EDTA/PBS, 20 minutes at 37° C.) and more dense structures including ILCC, etc were cultured in fibrin (Beattie, et al, 2002). Following 27 days in culture within fibrin, dispersed single cells were isolated by digestion in Accutase™ (15 minutes at 37° C.) and cultured in VitroPlus II growth medium (Vitro Diagnostics, Inc, Catalog Number VC03014) supplemented to 5% FBS and 10 nM GLP1. The following table provides a summary of the conditions of origin for the cell lines used in this study.

TABLE II

ORIGIN OF BETA ISLET PROGENITOR CELL LINES

| Cell Line | Culture Origin | Pass Number | ILCC (+/−) | Days in GM | Days in Nic | Ep-CAM IMS |
|---|---|---|---|---|---|---|
| VIT2 | VIT1 | 13 | + | 10 | None | Yes |
| VIT3 | VIT1 | 5 | + | 15 | 3 | Yes |
| VIT4 | VIT1 | 14 | + | 9 | 4 | Yes |
| VIT5 | Primary HP | 7 & 9 | + | 120 | None | No |

Abbreviations:
ILCC, islet-like cell clusters (See Results, FIG. 3);
Ep-CAM IMS, immunomagnetic separation based on monoclonal antibodies to the epithelial marker,
Ep-CAM, GM growth medium,
HP human pancreas,
Nic 10 mM nicotinamide.

The attachment dependent VIT2, VIT3, VIT4 cell lines were grown to approximate confluence, digested with Accutase™ (15 minutes at 37° C.) and sub-cultured at about 5,000 cells/cm² in VitroPlus II/10 nM GLP-1 using either 6-well plates (Cell Star) or T-25 flasks (Corning). These cell lines were continuously expanded using methods of cell growth analysis described above in example 2.

At early passage of the cell lines VIT2, VIT3, VIT4 & VIT5, limited dilution was used to establish clonal lines using 96-well plates and plating at 5 cells/well to account for plating efficiency, in 100 µl VitroPlus II/10 nM GLP-1. Only those wells containing single colonies were further expanded to pass 2 (single wells, 48-well plate) and pass 3 (one or two T-25 flasks and two wells of 48-well plates for IHC of insulin and glucagon) using transfer methods to prevent cross-contamination. Confluent, pass 3 cultures were digested in Accutase™, washed in PBS, resuspended in 1× cryopreservation medium (Vitro Diagnostics, Inc, Catalog Number VC03017) at about 5 million cells/ml, frozen at 1° C./minute to −80° C. and transferred to liquid nitrogen within 24 to 72 hours.

Insulin and glucagon were localized in various cultures of the VIT2, VIT3, VIT4 & VIT5 cell lines and their clonal derivatives by fixation of cells cultured in 48-well plates in 1% glutaraldehyde, overnight incubation with insulin MAB (Sigma Chemical Co, Catalog Number 12018) at 1/1000 dilution or glucagon MAB (Sigma Chemical Co, Catalog Number G2654) at 1/2000 dilution, both in PBS, followed by washout and incubation with an HRP-conjugated secondary antibody (Goat-anti-mouse-HRP; Jackson ImmunoResearch Laboratories, Inc., Catalog Number 115-035-062) at 37° C. for 30 minutes. Following washout of the secondary antibody, the cells were then incubated for 15 minutes in diaminobenzidine (Sigma Chemical Co, Catalog Number D-4293), and the stained cultures were examined by phase-contrast microscopy and photographed.

Figure 2:
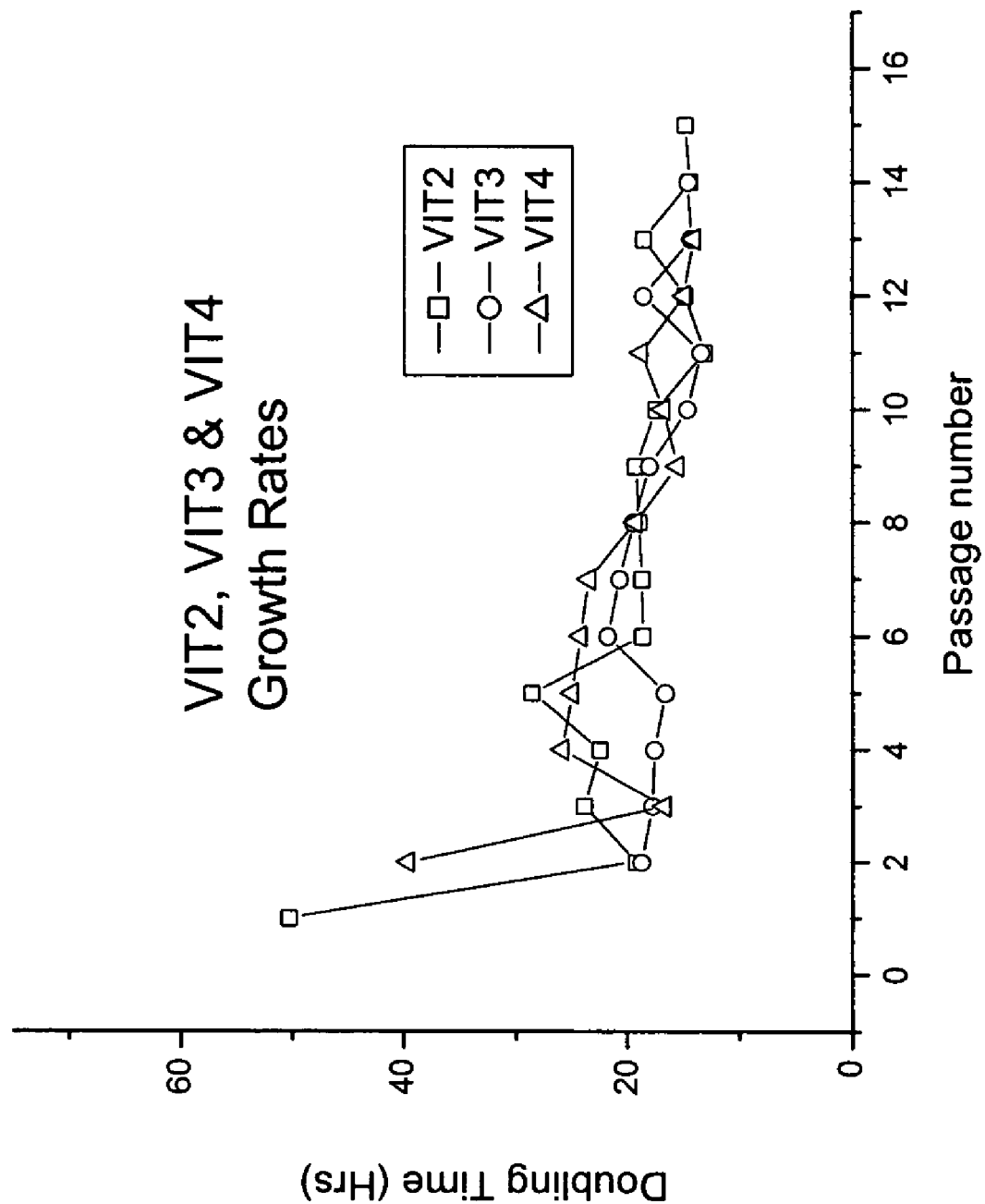
FIG. 2 shows growth rate analysis of the VIT2, VIT3 and VIT4 cell lines. Doubling time in hours is plotted as a function of passage number. The different plots shown reflect the cell lines, VIT2, VIT3 and VIT4. The number of population doublings is calculated as described and discussed in example 3.

The growth rate of the VIT2, VIT3 and VIT4 cell lines is shown in FIG. 2 as a function of passage number. These cell lines grew slowly in the initial passage; the doubling time was 45 to 130 hours, and then more rapidly in later passages. VIT2 and VIT4 cells divided at an intermediate rate from passage 3 to about 8 and thereafter exhibited relatively rapid growth comparable to VIT3 cells, doubling time, $t_d$ averaged about 16 hours with a 12 to 18 hour range. The total number of population doublings calculated as described in the methods was 73.5, 74 and 59 for the VIT2, VIT3 and VIT4 cell lines, respectively.

The parental VIT1 cell line exhibits similar growth characteristics including a maintained doubling time of about 17 hours from passage 15 to 26, approximately 130 population doublings, as shown in FIG. 1. Since mortal human fetal cell lines have the capacity to double only about 50 times (Hayflick, 1985), the maintained expansion of the VIT2, VIT3 and VIT4 cell lines through 59 to 74 population doublings suggests apparent immortality.

FIG. 3 shows phase contrast images of early pass VIT2 & VIT3 cells. In FIG. 3A, VIT3 cells are shown at 100× prior to appearance of ILCC (FIG. 3B). The attached small cells (~10-15 µm in diameter) shown in 3A and 3B generate the associated ILCC, on top of the cell monolayer as shown in center of the field in FIG. 3B. ILCC consist of a diffuse cluster of nearly spherical cells that are loosely associated with the underlying, attached cells. FIG. 3C shows VIT2 cells in passage 4 without associated ILCC. These cells contain clear-core vesicles, while cytoplasmic dense-core vesicles characterize the VIT3, VIT4 and VIT5 cells. FIG. 3D shows ILCC in a culture of VIT2 cells that was stained for insulin as described above. Since insulin-containing cells could be detected within the ILCC, (FIG. 3D), this suggests that the ILCC may contain human beta cells. In those cells which stained positive for insulin (about 5 to 10% of the cell population) the reaction product was clearly localized to the cytoplasm of the cell without significant nuclear staining (FIG. 3D). Also, at higher magnification, the insulin appeared to be localized to secretory vesicles within the cells (not shown), possibly insulin-containing vesicles of beta cells.

Ep-CAM-positive cells were isolated from primary cultures of the mesenchymal cell line VIT1 that had been exposed to GLP-1 for sufficient period to induce epithelial cells. Immunomagnetic separation using an antibody specific to Ep-CAM resulted in the generation of the cell lines VIT2, VIT3 and VIT4. These lines exhibited similar growth rates and expansion capabilities as the parental VIT1 cell line. Exposure of the VIT2 cell line to GLP-1 also resulted in the appearance of loosely associated ILCC and some of the cells within the ILCCs were positive for insulin, suggesting the presence of human beta cells within the VIT2-derived ILCCs. Limited dilution cloning and subsequent expansion was used to establish clonal cell lines.

Example 5

Differentiation of Human Beta Islet Cells from Progenitor Cell Lines

As described in example 4, the human pancreatic epithelial cell lines, VIT2, VIT3 and VIT4 were used to establish clonal cell lines by limiting dilution. The working hypothesis was that these clonal cell lines may allow establishment of fully differentiated cells that compose the human beta islet, i.e., alpha, beta, delta and PP endocrine cells, since the clones were established from Ep-CAM positive cells isolated from VIT1 cultures under conditions known to induce the generation of epithelial cells, including presumptive beta cells containing human insulin. However, initial observations described in example 4 suggested that contrary to expectation, the clonal cell lines exhibit properties of beta islet progenitor cells including an ability to generate cells that express ILCC that were positive for insulin and expansion through at least 74 population doublings without apparent diminution in growth rate, suggesting self-renewal which was not expected if the cells were fully differentiated.

In this example, the capability of clonal cell lines derived from the VIT1 mesenchymal cell line to generate beta islet cells is subject to more detailed investigation. Nearly all of the clonal cell lines derived according to the methods described in example 4 were found to generate ILCC that contained cells positive for human insulin and human glucagon by IHC procedures. Conditions resulting in the differentiation of functional human beta cells were determined using qualitative hormone content analysis by IHC and basal as well as glucose-stimulated insulin secretion to measure effects of selected independent variables.

Immunohistochemical methods for the determination of insulin and glucagon in cultured cells were described in example 4, above. Glucose-stimulated insulin secretion was determined by modifications of the method described in example 1, above and is elaborated within the "Results" section of this example.

Table II, below, shows the various clonal cell lines that were generated together with the results of immunohistochemical analysis for insulin and glucagon. The nomenclature used for these cell lines is the initial designation of the parental cell line, e.g., VIT2 followed by the well number (96-well plate) from which the clonal cell line was derived.

TABLE III

CLONAL CELL LINES DERIVED FROM VIT2, VIT3, VIT4 AND VIT5 CELLS AND THE RESULTS OF IHC STAINING FOR INSULIN AND GLUCAGON

| Cell Line | Glucagon-Small cell | Glucagon-ILCC | Insulin-Small cell | Insulin-ILCC |
|---|---|---|---|---|
| VIT2-A2 | +++ | ++ | + | ++ |
| VIT2-A11 | ++ | − | − | + |
| VIT2-B4 | ND | ND | ND | ND |
| VIT2-C12 | ++ | ++ | − | + |
| VIT2-G1 | ++ | ++ | + | ++ |
| VIT2-G6 | ND | ++ | ND | + |
| VIT2-H9 | − | ++ | − | ++ |
| VIT3-B4 | − | +++ | − | ++ |
| VIT3-C8 | ND | +++ | ND | +++ |
| VIT3-F1 | − | ++ | − | ++ |
| VIT3-F4 | − | + | − | + |
| VIT3-F7 | − | + | − | ++ |
| VIT3-G12 | − | ++ | − | +++ |
| VIT3-H11 | − | ++ | − | ++ |
| VIT4-C4 | ND | +++ | − | ++ |
| VIT4-D10 | − | +++ | − | +++ |
| VIT4-F9 | − | ++ | − | ++ |
| VIT4-G9 | − | +++ | − | +++ |
| VIT4-H9 | − | ++ | − | + |
| VIT5-D12 | − | ++ | ND | ++ |
| VIT5-H2 | − | ++ | − | + |
| VIT5-H9 | − | ++ | − | + |
| VIT5-H12 | − | ++ | − | ++ |

Key to Table III:
+: About 5% of the cell population is positive;
++: About 10% of the cell population is positive;
+++: About 20% of the cell population is positive;
−: No positive staining was detected;
ND: Not determined due to low cell number or masking of small cells by ILCC.

The results shown in Table III summarize the IHC examination of 23 different clonal cell lines derived from the mixed epithelial cell lines VIT2, VIT3, VIT4 and VIT5 as described above in example 4. The relative reactivity to the insulin or glucagon antibody in ILCC refers to the reactivity observed within ILCC that were derived from underlying, attached clonal cells shown in FIGS. 3B and 3D. Small cell reactivity refers to the underlying, attached cells from which ILCC were derived. Visualization of these cells was sometimes obscured by the overlying ILCC yielding designation of ND (not determined) in table III. (The cell line VT2-B4 was ND due to lack of growth in these cultures because of an insufficient number of cells.) The results shown in Table III indicate that ILCC derived from the clonal cell lines were nearly always positive for glucagon and insulin at about 5% (+), 10% (++) or 20% (+++) of the total cell population of the ILCCs. The non-determinant result from clone VIT2-B4 is due to an insufficient number of cells present to yield viable cultures. ILCC derived from clone VIT2-A11 were negative for glucagon and positive for insulin, suggesting possible preferential derivation of ILCC containing beta cells from this clone. However, the consistent observation that ILCC were positive for both insulin and glucagon also supports the hypothesis that the clonal cell lines are beta islet progenitor cell lines rather than terminally differentiated beta islet cells, since clonal cell lines may be induced to form two different cell types that comprise the Islets of Langerhans, i.e., presumptive alpha cells containing glucagon and beta cells containing insulin. These results support the hypothesis that the clonal cell lines are beta islet progenitor cell lines capable of at least multi-potent differentiation into more than one cell type.

Cultures of the clonal cell lines shown in table III are initially established as multi-cellular colonies of monolayer, epithelial-like cells 10-15 μm in diameter that continually divides and eventually reaches confluence. It is typically possible to visualize stained cells of both ILCC and the underlying monolayer ("small cell" in table III) while occasionally the ILCC were sufficiently extensive to obscure the underlying monolayer cells (most NDs in table II). The small cells of the clonal cell lines were generally negative or ND for insulin or glucagon, 90% or 83%, respectively while 10% and 17% of the clones showed small cell positivity for insulin and glucagon, respectively. Also, when positive, a greater percentage of the small cell population was glucagon positive as compared to insulin. These cultures also contained occasional larger cells (20 to 30 μm in diameter) that nearly always were positive for insulin and glucagon (not shown).

One of the clonal cell lines examined above, VIT4-G9, showed a greater frequency of generation of ILCC than other clones and the ILCC express both glucagon and insulin strongly by IHC analysis (Table III). The clonal cell line VIT4-G9 was therefore subject to additional studies of its capability to generate human beta islet cells.

A general principle of developmental cell biology is that cellular differentiation and growth are at least partially exclusive of each other. High rates of cellular proliferation usually occur in the absence of differentiation, while differentiation usually requires quiescence or low rates of cell proliferation. Initial observations of the clonal cell line VIT4-G9 were consistent with this concept since pancreatic hormone-containing ILCC only appeared at later stages of culture following slower cell growth as a consequence of confluence and possibly contact inhibition. Also, additional preliminary studies showed that addition of 10 mM nicotinamide, a well-known beta islet differentiation agent, increased the prevalence of ILCC by about 5-fold while also inducing nearly quiescent cultures. Furthermore, prior studies of the induction of ILCCs in VIT1 cells showed that the growth factor GLP-1 greatly increased the frequency of ILCC generation and these ILCC were shown to contain insulin (example 3, above) by IHC procedures. Hence, the ability to derive beta islet cells from VIT4-G9 cells was determined under conditions where an initial growth phase in the presence of various growth factors was followed by a period of slow growth with or without addition of differentiation factors.

Figure 4:
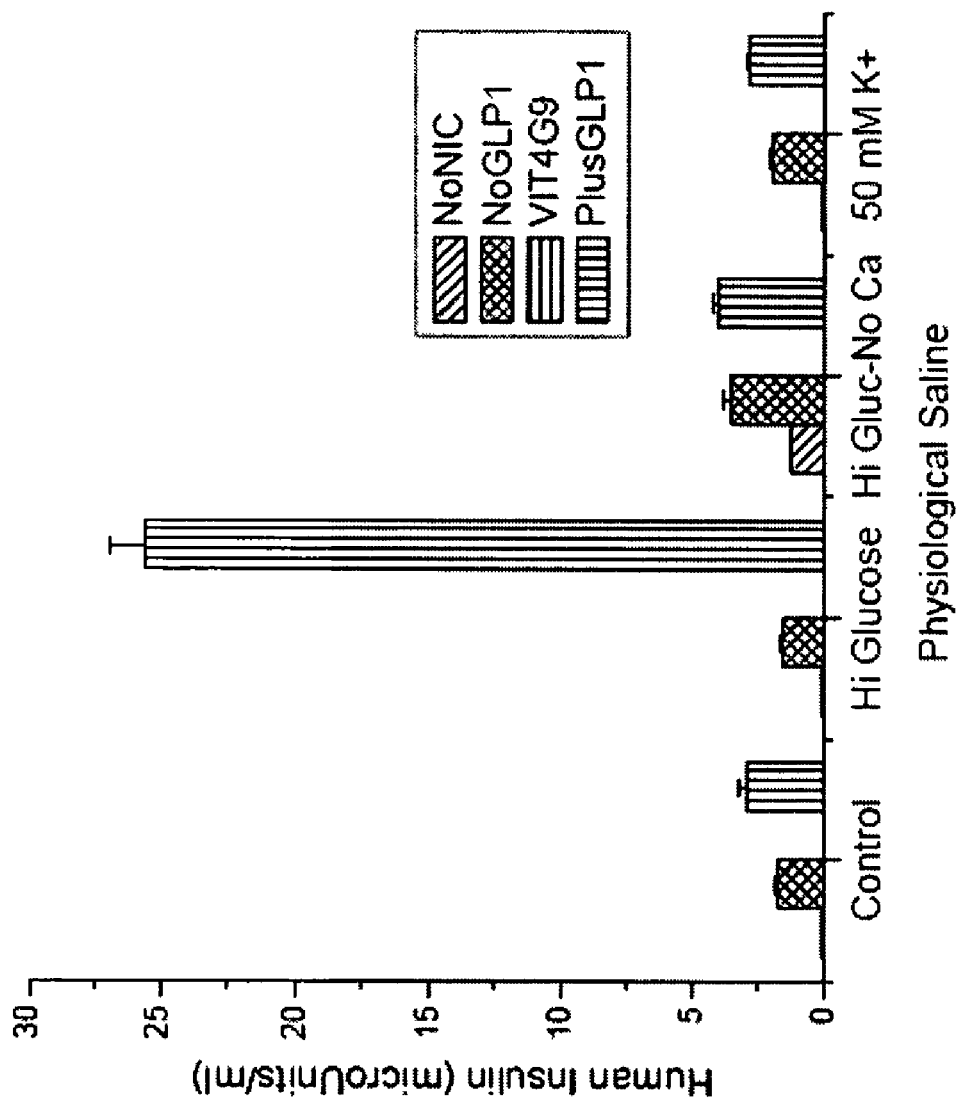
FIG. 4 shows human insulin secretion from VIT4-G9 cultures that were subject to different culture conditions prior to acute incubation in physiological saline solutions as described in example 5. Insulin secretion is shown as concentration (μU/ml; mean+/−SD of 4 determinations) within physiological saline solutions collected from cultures exposed to various different conditions of growth and differentiation.

While previous studies have demonstrated presence of insulin and glucagon within ILCC derived from VIT4-G9 cells (e.g., Table II), insulin secretion and its potential regulation by extracellular glucose levels provide additional information about the differentiation of functional beta cells. For example, glucose-stimulated insulin secretion requires expression of functional glucose transporter protein and glucokinase in addition to insulin. Thus, additional studies involved determination of insulin secretion after exposure of cultures of VIT4-G9 cells to various growth conditions followed by differentiation conditions. The results of such experiments are shown in FIG. 4. The growth/differentiation conditions tested are as follows: a) No NIC: 5 days in VitroPlus II/GLP-1 followed by five days in serum-free VitroPlus II (VitroPlus II contains 2% FBS); b) No GLP1: 5 days in VitroPlus II followed by 6 days in 0.5% FBS VitroPlus II+10 mM nicotinamide; c) VIT4-G9: Pass 16 VIT4-G9 in VitroPlus II (Previously in continuous culture through 12 passages); d) Plus GLP1: 5 days in VitroPlus II/GLP-1 followed by 6 days in 0.5% FBS VitroPlus II+10 mM nicotinamide. Samples were collected for insulin assay by acute incubation of 250,000 dispersed cells in physiological saline for 90 minutes incubation (See example 1 for additional methodological details). As shown in FIG. 4, when VIT4-G9 cells were cultured in VitroPlus II/GLP-1 for 5 days followed by culture in low serum VitroPlus II containing 10 mM nicotinamide this resulted in cells that exhibited basal secretion of insulin (control). The rate of insulin secretion was substantially increased when these cells were exposed to 20 mM Glucose in saline containing 5 mM $Ca^{2+}$ (Hi Glucose). This glucose-stimulated increase in insulin secretion was predominantly, although not entirely, eliminated in the absence of added $Ca^{2+}$ (+1 mM EDTA) (Hi Gluc-No Ca) and exposure to 50 mM K+ did not significantly increase insulin secretion above control levels. VIT4-G9 cells that were proliferating without exposure to differentiation conditions showed no measurable insulin secretion under all conditions investigated, indicating the necessity of differentiation conditions for the induction of basal and glucose-stimulated insulin secretion. The presence of nicotinamide in the differentiation phase was necessary for glucose-stimulated insulin secretion even though serum-free VitroPlus II also resulted in nearly quiescent cultures. The presence of GLP-1 was also necessary during the growth phase. The results of these experiments show that growth of the VIT4-G9 cell line in VitroPlus II/GLP-1 for 5 days followed by differentiation in low serum VitroPlus II containing 10 mM nicotinamide for 6 days resulted in the differentiation of cells that secrete basal levels of insulin and significant calcium-dependent, glucose-stimulated insulin secretion.

IHC studies of glucagon and insulin distribution in cultures of VIT4-G9 cells were also conducted to repeat and extend results shown in table III. ILCC were derived in cultures where VIT4-G9 cells were expanded during a growth phase followed by differentiation conditions during slow growth according to similar procedures as used to differentiate insulin-secreting cells as described above. In general these growth conditions also resulted in ILCC that were positive for both insulin and glucagon at the $9^{th}$ passage (insulin) and at the $16^{th}$ passage (insulin & glucagon), indicating that VIT4-G9 cells may be differentiated into hormone-positive ILCC at passages 3 (table III), 9 and 16. While those conditions that result in differentiation to functional beta cells, as indicated by basal and calcium-dependent glucose stimulated insulin secretion, also resulted in ILCC that were positive for insulin and glucagon by IHC, it is also apparent that hormone positive ILCCs were derived under conditions that did not also result in insulin secretion (e.g., VIT4-G9 cultures used to derive the results shown in table III did not involve use of a differentiation phase). This indicates that hormone presence appears earlier in the differentiation process than other cellular systems necessary for insulin secretion such as the glucose transporter (cf. Edlund, 2001).

In summary, while it was theorized that clonal cell lines resulting from isolation of VIT1 epithelial cells from cultures induced to form insulin-containing cells would allow isolation of the differentiated cells comprising the beta islet, the evidence presented here supports the hypothesis that these cell lines are multi-potent progenitors of human beta islet cells. This evidence includes:

1. Both insulin and glucagon were detected within ILCC derived from several different clonal cell lines (Table III). If these clones were fully differentiated beta islet cells, only a single hormone would be expressed within a clonal cell line.
2. Exposure of the clone VIT4-G9 to specific conditions of growth followed by differentiation without growth resulted in basal and calcium-dependent, glucose-stimulated insulin secretion while other conditions failed to yield basal or glucose-stimulated insulin secretion. Generation of fully differentiated cells would not require specific culture conditions to generate functional beta islet cells.
3. Insulin is expressed within ILCC derived from VIT4-G9 cells prior to the development of insulin secretion capability, again indicating incomplete development rather than derivation of fully differentiated beta cells.
4. Mixed epithelial cell lines, VIT2, VIT3 and VIT4 expand at a rapid growth rate exceeding the number of population doublings of mortal cells, indicating apparent immortality. Fully differentiated cells are typically quiescent or expand at a slow rate for a limited number of population doublings.
5. Insulin and glucagon were demonstrated within ILCCs derived from VIT4-G9 cells at passages 3, 9 and 16, indicating developmental capability at various growth stages that is incompatible with a fully differentiated cell type.

Taken together, the available evidence supports the hypothesis that the clonal cell lines listed in table III are beta islet progenitor cells capable of programmed differentiation into at least alpha and beta cells in response to appropriate environmental conditions. These progenitor cells may also be pluripotent, although this property has not yet been demonstrated. The control cell line VIT5 derived from primary human pancreatic cell cultures also exhibited similar ability to generate ILCC that express both insulin and glucagon (Table III). Clonal cell lines may specifically express the alpha or beta cell phenotype within ILCC (e.g., VIT2-A11). Progenitor cell lines with limited capacity to generate multiple hormone phenotypes may thus exist. Exposure to nicotinamide in combination with GLP-1, and other members of the PACAP/glucagon superfamily may be a critical factor in affecting the differentiation capacity of beta islet progenitor cell lines.

A process is described that results in the differentiation of functional human beta islet cells from the progenitor cell line known as VIT4-G9. The process of differentiation includes exposure of progenitor cell lines to: a) A growth period of approximately 5 days wherein the cells are exposed to GLP-1 at appropriate levels, followed by: b) a differentiation period of about 5 days wherein the cells are exposed to growth medium containing reduced serum levels and 10 mM nicotinamide.

Example 6

Characterization of Beta Islet Progenitor Cell Lines

This section describes results of additional characterization of beta islet progenitor cell lines that are described in the previous examples. Additional growth analysis and gene expression profiling results are presented. This analysis also provides additional evidence supporting the hypothesis that the progenitor cell lines have properties of stem cells.

Growth analysis methods have been previously described. Cyclopamine (LC Laboratories, Catalog number C-8700) was prepared at 20 mM in ethanol, stored at −20° C. and added to cultures as indicated in the results. Gene expression profiling was conducted using a total RNA sample was derived according to the RNeasy® protocol for animal cells (Qiagen) from VIT1 cells during passage 4, i.e., during earlier passages where doubling time was about 30 hours. This sample was amplified to generate cRNA that was biotinylated, fragmented and hybridized to the Amersham CodeLink Human UniSet 1 microarray containing 20K probes to human genes. This study was performed in collaboration with Dr. Zolton Szallasi and his colleagues at Harvard University and its affiliates. The resulting expression data was sorted according to intensity and those genes exhibiting greater than threshold intensity (0.287724) were subject to gene microarray pathway profiling (Dahlquist, et al., 2002) by bioinformatic methods.

Growth rate analysis of the VIT4-G9 clonal cell line is shown in FIG. 5. This cell line has been expanded through 25 passages while maintaining relatively rapid growth (Mean+/− SD $t_d$ 16.9+/−1.61 Hrs) corresponding to 130 population doublings. The growth characteristics of the VIT4-G9 cell line are comparable to the parental VIT1 cell line (FIG. 1) including slower growth rates initially followed by more rapid and sustained growth through multiple passages. The VIT1 cell line has been expanded through 130 population doublings and the VIT4-G9 cell line has also been expanded through 130 population doublings without indication of significant growth rate change. As noted previously, the lack of senescence after 50 population doublings, the observed maximum doubling capacity of mortal cells (Hayflick, 1985), is evidence of apparent immortality of both the VIT1 and VIT4-G9 cell line.

As described below, gene expression profiling of the VIT1 cell line provides additional evidence for stem cell properties of this line, including apparent activation of two pathways thought to be central determinants of stem cell self-renewal, the Wnt and Hedgehog (Hh) pathways. In the results shown in FIG. 5, additional evidence for involvement of the Hh pathway in controlling growth of the VIT4-G9 cell line is presented. The effects of cyclopamine, a specific inhibitor of Smo (smoothened) and overall activation of the Hh pathway (e.g., Tsonis, et al, 2004) was determined. At 10 μM cyclopamine, VIT4-G9 growth slowed substantially. The doubling time was increased from 17.5 hours to about 50 hours. Also, VIT4-G9 growth was blocked exposure to 20 μM cyclopamine since fewer cells than plated were detected after 2-weeks in culture (Data not shown.) The reduction in growth rate by cyclopamine was dose dependent since at 5 μM cyclopamine, the growth rate decrease was considerable less. Doubling time slowed to 20 hours (16.5 hours untreated) that was maintained during 3 successive passages (FIG. 5). The implication of these results regarding the mechanism of apparent immortality of the VIT4-G9 cell line is discussed below.

Gene expression profiling of VIT1 cells that were used to derive the VIT2, VIT3 and VIT4 cell lines using the CodeLink microarray (Amersham) showed that 14,842 genes were expressed at levels that were greater than threshold out of a total of 20,000 human genes detectable with this array. The results of this analysis are discussed herein with particular emphasis on those genes thought to be characteristic of stem cells as well as an analysis of the genetic expression profile relative to cell type rather than a comprehensive review of the entire gene expression profile of the VIT1 cells. Also, the VIT1 cell line was parental to additional cell lines (Table II & III) wherein previously described data indicates properties of human beta islet progenitor cell lines. Thus, gene expression profiles, for example within the VIT4-G9 cell line, may be altered as a consequence of the methods used to induce expression of epithelial markers, purification and expansion of the cell lines.

Profiling of several biological pathways indicated significant gene expression within VIT1 cells. Key components of the cell cycle, apoptosis, integrin-mediated cell adhesion and the N-glycan biosynthesis pathway were expressed within VIT1 cells. Also, VIT1 cells express 25 of 32 genes that are characteristic of long-term hematopoietic stem cells (Ivanova, et al., 2002) and several known homeobox genes (~65 genes). These genes are key molecular switches in programming the expression of a series of genes underlying specific phenotypic properties. Members of the Hox family of homeobox genes were particularly prevalent (20 genes) including the 1, a, b, c and d clusters. Hox genes are important in development of the nervous system, axial skeleton, limbs and several organ-specific development patterns and are also known to be critically important to hematopoiesis (Goodman and Scambler, 2001; Lawrence, et al., 1996). The expression of a variety of different homeobox genes within the VIT1 cells suggests that these cells retain developmental capacity for differentiation into a variety of different cell types, including epithelia cells that comprise beta islets. Plurapotentiality of the VIT1 cells is also suggested by expression of markers for cardiac muscle (isll), a variety of neuronal components including dopaminergic, serotoninergic, adrenergic, opiod and acetylcholine neurotransmitter systems and developmental genes, together with fibroblast-related genes as well as genes related to development of beta islets including for example, Pdxl. It should also be noted that isll expression is also related to specification of endocrine cell development (Jenson, 2004). Furthermore, human mesenchymal cells derived from adult marrow exhibit pluripotency (Jiang, et al, 2002) and VIT1 cells share several characteristics of adult mesenchymal stem cells.

In addition, gene expression profiling provides additional evidence supporting the mesenchymal nature of the VIT1 cell line. As noted above, these cells express phenotypic markers characteristic of mesenchymal cells (vimentin and $CD_{90}$) and were negative for markers characteristic of epithelial cells, Ep-CAM, E-cadherin and cytokeratins AE1/AE3, by immunohistochemical analysis. Gene expression profiling also revealed high intensity expression of vimentin (286.8 of 300 maximum) and a Thy-1-related gene (cDNA FLJ25136, clone CBR07030, highly similar to Thy-1 membrane glycoprotein precursor). Furthermore, additional genetic markers of mesenchymal cells including bone morphogenic protein receptors Type 1B and Type 1A, $CD_{44}$ as well as various fibroblast growth factors (Nos. 1, 2, 5, 6, 8, 9, 11, 18, 20, 21, and 23) together with FGF Receptor-like 1 and FGF receptor 3 were also expressed in VIT1 cells. On the other hand, markers of endodermal cells, from which pancreatic endocrine cells are derived during development, were not expressed in VIT1 cells, including Soxl7 and AFP, while GATA4 and GATA6 were expressed. Taken together, the expression of multiple mesenchymal markers at the near exclusion of endodermal cell markers supports the mesenchymal nature of the VIT1 cell line and provides a further distinction of the present invention from the previously known processes of the development of pancreatic beta islet cells.

Key genes of the Wnt pathway are also expressed within the VIT1 cell line including receptors, notably Frizzled 7 (41.56 intensity), Wnt ligands, especially Wnt 5B (31.8 intensity), together with key intracellular components of the Wnt signaling pathway. GSK3 beta (13.3) and APC (1.74) are expressed and beta-catenin expression was at sub-threshold intensity levels (0.08). C-myc is expressed at relatively high intensity levels (~18.5). It is thus apparent that Wnt pathway is activated in VIT1 cells, possibly through elevated Wnt 5B expression for example, resulting in de-repression of the transcription factors, Tcf-1/Lef leading to elevated c-myc expression which drives cell proliferation and possibly other effects of c-myc expression as well as increased expression of other genes controlled by Tcf-1/Lef. Also, certain key genes of the human Hedgehog (Hh) signaling pathway including agonists (desert Hedgehog homolog), receptors, (Ptch2 & Hedgehog interacting protein) and transcription factors (Gli2 & Gli3) were expressed in VIT1 cells. Hh pathway activation contributes to stem cell self-renewal and immortality by inhibition of apoptosis through elevated Fas ligand expression (Lum and Beachy, 2004).

The activation of both the Wnt and Hedgehog signaling pathways has been implicated in the maintenance of stem or progenitor cells in a variety of tissues including skin, blood, gut, prostate and the nervous system (Beachy, et al, 2004). The apparent activation of these pathways in the VIT1 cells suggests that activation of the Wnt and Hh signaling pathways may also be involved in the maintenance of proliferation of pancreatic progenitor or stem cells described in the present invention. Also, since the VIT2, VIT3 & VIT4 cell lines derived through Ep-CAM IMS of VIT1 cells exhibit continued expansion through at least 74 population doublings and the clonal cell line VIT4-G9 has been expanded through 130 population doublings, these cells are apparently immortal and self-renewing which is a characteristic property of progenitor or stem cells. Indefinite proliferation may be driven by activation of the Wnt and Hh signaling pathways, as this is a possible mechanism of the apparent immortality of the parental VIT1 cell line and the derivative cell lines are also likely to express Wnt and Hh pathway activation.

The effects of cyclopamine on growth of VIT4-G9 cells provide more direct evidence for the involvement of the human Hh pathway in self-renewal. As shown in FIG. 5, cyclopamine produced a dose-dependent reduction in growth rate (increase in doubling time). Since cyclopamine is known to specifically interfere with smoothened (Smo) and thus inactivate the Hh pathway (e.g., Tsonis, et al, 2002), the reduction in growth rate by cyclopamine indicates that Hh activation is an important component of the mechanism of rapid and sustained growth of the VIT4-G9 cell line. This effect may be mediated by inhibition of apoptosis through elevated Fas ligand expression ((Lum and Beachy, 2004) since at higher levels of cyclopamine, cell growth was blocked and cell numbers regressed indicating a predominance of apoptosis. Evidence showing expression of Hh pathway components in VIT1 cells and the dose-dependent reduction in VIT4-G9 cells by cyclopamine also distinguish the present invention from known developmental pathways leading to derivation of terminally differentiated beta islet cells since endodermal cells destined to become pancreatic progenitor cells do not express hedgehog signaling molecules (Edlund, 2001)

In summary, further characterization studies of the VIT1 and VIT4-G9 cell lines provide additional evidence for stem/progenitor cell properties. Gene expression profiling indicates expression of a variety of human genes characteristic of hematopoietic stem cells together with numerous homeobox genes that are known to control cell lineage determination during development. Furthermore, pluripotential development capability is suggested by expression of genes involved in development of a variety of different cell types including cardiac muscle, several neuronal cells, pancreatic beta islets and fibroblasts. Finally, the Wnt and hedgehog pathways that are known to maintain stem cell self-renewal, cellular differentiation and a variety of other cellular activities are active within these cells as indicated by gene expression profiling and the effects of cyclopamine, a specific hedgehog pathway antagonist. Cyclopamine results in a dose-dependent decrease in the growth rate of VIT4-G9 cells indicating that activation of the hedgehog pathway maintains the rapid and sustained growth of these cells probably by inhibition of apoptosis. Gene expression profiling shows the expression of several markers characteristic of mesenchymal cells while known endodermal cell markers are not expressed in VIT1 cells, further supporting the mesenchymal nature of this cell line.

LITERATURE CITED

1. Beachy P A, Karhadkar S S and Berman D M, Tissue repair and stem cell renewal in carcinogenesis. Nature 432: 324-331, 2004.

2. Dahlquist K D, Salomonis N, Vranizan K, Lawlor S C and Conklin B R, GenMAPP, a new tool for viewing and analyzing microarray data on biological pathways. Nature Genetics 31: 19-20, 2002.

3. Davies J A, Mesenchyme to epithelium transition during development of the mammalian kidney tubule. Acta Anat (Basel) 156: 187-201, 1996.

4. Davies J A, Perera A D and Walker C L, Mechanisms of epithelial development and neoplasia in the metanephric kidney. Int J Dev Biol 43: 473-478, 1999.

5. Doyle M E and Egan J M, Glucagon-like peptide-1. Recent Prog Horm Res 56: 377-399, 2001.

6. Edlund H, Beta cell differentiation and growth: Developmental biology of the pancreas. Diabetes 50 (Suppl. 1): S5-S9, 2001.

7. Friedman D L, Role of cyclic nucleotides in cell growth and differentiation. Physiol Rev 56: 652-708.

8. Garcia-Ocana A, Takane K K, Syed M A, Philbrick W M, Vasavada R C and Stewart A F, Heptocyte growth factor overexpression in the islet of transgenic mice increases beta cell proliferation, enhances islet mass and induces mild hypoglycemia. J. Biol. Chem 275: 1226-1232, 2000.

9. Goodman F R and Scambler P J, Human HOX gene mutations. Clin Genet, 59: 1-11, 2001.

10. Hayflick L, The cell biology of aging. Clin Geriatr Med 1: 15-27, 1985.

11. Hori Y, Rulifson I C, Tsai B C, Heit J J, Cahoy J D, and Kim S K, Growth inhibitors promote differentiation of insulin-producing tissue from embryonic stem cells. Proc NBatl Acad Sci USA 99: 16105 -16110, 2002.

12. Ivanova N B, Dimos J T, Schaniel C, Hackney J A, Moore K A and Lemischka I R, A stem cell molecular signature. Science 298: 601-604, 2002.

13. Jiang Y, Jahagirdar B N, Reinhardt R L, Shwartz R E, Keene C D, Ortiz-Gonzalez X R, Reyes M, Lenvak T, Lund T, Blackstad M, Du J, Aldrich S, Lisberg A and Low W C, Pluripotency of mesenchymal stem cells derived from adult marrow. Nature 418: 41-49, 2002.

14. Jensen J, Gene regulatory factors in pancreatic development. Developmental Dynamics 229: 176-200, 2004.

15. Lawrence H J, Sauvageau G, Humphries R K and Largman, C, The role of HOX homeobox genes in normal and leukemic hematopoiesis. Stem Cells 14: 281-291, 1996.

16. Lum L and Beachy P A, The Hedgehog response network: sensors, switches and routers. Science 304: 1755-1759, 2004

17. Macera-Bloch L, Houghton J, Lenahan M, Jha K K, and Ozer H L, Termination of lifespan of SV40-transformed human fibroblasts in crisis is due to apoptosis. J Cell Physiol 190: 332-344, 2002.

18. McEvoy R C, Thomas N M, Bowers C and Ginsberg-Feller F, Maintenance of fetal human pancreatic beta cells in tissue culture. Medical Biology 64: 271-276, 1986.

19. Mngomezulu W T, Kramer B, Beneficial effect of nicotinamide on the proportion of insulin cells in developing chick pancreas. Dev Growth Differ 42: 187-193, 2000.

20. Montalto M C, Phillips J S and Ray F A, Telomerase activation in human fibroblasts during escape from crisis. J Cell Physiol 180: 46-52.

21. Poy M N, Eliasson L, Krutzfeldt J, Kuwajima S, Xiaosong M, MacDonald P E, Pfeffer S, Tuschl T, Rejewsky N, Rorsman P and Stoffel M, A pancreatic islet-specific microRNA regulates insulin secretion. Nature 432: 226-230, 2004.

22. Ryan E A, Lakey J R T, Ray V R, Korbutt G S, Kin T, Imes S, Rabinovitch A, Elliott J F, Bigam D, Kneteman N M, Warnock G L, Larsen I and Shapiro A M J, Clinical outcomes and insulin secretion after islet transplantation with the Edmonton protocol. Diabetes 50: 710-719, 2001.

23. Saalbach A, Aust G, Haustein U F, Herrmann K, and Anderegg U, The fibroblast-specific MAb AS02: a novel tool for detection and elimination of human fibroblasts.

24. Shapiro A M, Lakey J R, Ryan E A, Korbutt G S, Toth E, Warnock G L, Kneteman N M, Rajotte R V, Islet transplantation in seven patients with type 1 diabetes mellitus using a glucocorticoid-free immunosuppressive regimen. N. Engl. J Med 343: 289-290, 2000.

25. Shiroi A, Yoshikawa M, Yokata H, Fukui H, Ishizaka S, Tatsumi K and Takahashi Y, Identification of insulin-producing cells derived from embryonic stem cells by zinc-chelating dithizone. Stem Cells 20: 284-292, 2002.

26. Soresnson R L and Brelje T C, Adaptation of islets of Langerhans to pregnancy: beta-cell growth, enhanced insulin secretion and the role of lactogenic hormones. Horm Metab Res 29: 301-307, 1997.

27. Stein, G H, SV40-transformed human fibroblasts: evidence for cellular aging in pre-crisis cells. J Cell Physiol 125: 36-44, 1985.

28. Tsonis P A, Vergara M N, Spence J R, Madhavan M, Kramer E L, Call M K, Santiago W G, Vallance J E, Robbin D J, and Del Rio-Tsonis K, A novel role of the hedgehog pathway in lens regeneration. Dev Biol 267: 450-461, 2004.

Each publication cited herein is incorporated herein by reference in its entirety.

Those well skilled in the art will recognize that there are additional embodiments and derivatives of the present invention, which is not to be limited to the above-described examples. While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated cell, comprising cell line VIT4-G9, deposited under ATCC Accession number PTA-8683.

* * * * *